US008439036B2

(12) United States Patent
Winter et al.

(10) Patent No.: US 8,439,036 B2
(45) Date of Patent: *May 14, 2013

(54) EXHALATION VALVE ASSEMBLY WITH INTEGRAL FLOW SENSOR

(75) Inventors: David Phillip Winter, Encinitas, CA (US); Warren G. Sanborn, Escondido, CA (US)

(73) Assignee: Covidien LP, Mansfield, MA (US)

( * ) Notice: Subject to any disclaimer, the term of this patent is extended or adjusted under 35 U.S.C. 154(b) by 545 days.

This patent is subject to a terminal disclaimer.

(21) Appl. No.: 12/628,803

(22) Filed: Dec. 1, 2009

(65) Prior Publication Data

US 2011/0126834 A1    Jun. 2, 2011

(51) Int. Cl.
*A62B 9/02* (2006.01)
*F16K 31/02* (2006.01)

(52) U.S. Cl.
USPC .............................. 128/205.24; 128/204.23

(58) Field of Classification Search ............ 128/200.24, 128/201.25, 202.22, 202.27, 204.18, 204.21, 128/204.23, 205.12, 205.23, 205.24, 205.27–205.29; 251/331, 291
See application file for complete search history.

(56) References Cited

U.S. PATENT DOCUMENTS

| | | | |
|---|---|---|---|
| 2,619,986 A * | 12/1952 | Goepfrich | ............. 251/129.17 |
| 3,444,857 A | 5/1969 | Godel | |
| 3,481,333 A | 12/1969 | Garrison | |
| 3,485,243 A | 12/1969 | Bird | |
| 3,500,826 A | 3/1970 | Haire | |
| 3,688,794 A | 9/1972 | Bird et al. | |
| 4,207,884 A | 6/1980 | Isaacson | |
| 4,241,756 A | 12/1980 | Bennett et al. | |
| 4,406,291 A | 9/1983 | Schwesinger | |
| 4,527,557 A | 7/1985 | DeVries et al. | |
| 4,587,967 A | 5/1986 | Chu et al. | |
| 4,608,976 A | 9/1986 | Suchy | |
| 4,699,137 A | 10/1987 | Schroeder | |
| RE32,553 E | 12/1987 | Bennett et al. | |
| 4,712,580 A | 12/1987 | Gilman et al. | |
| 4,727,871 A | 3/1988 | Smargiassi et al. | |
| 4,747,403 A | 5/1988 | Gluck et al. | |
| 4,752,089 A | 6/1988 | Carter | |
| D300,271 S | 3/1989 | Rudolph et al. | |

(Continued)

FOREIGN PATENT DOCUMENTS

| | | |
|---|---|---|
| EP | 0266963 | 5/1988 |
| EP | 0459647 | 12/1991 |

(Continued)

OTHER PUBLICATIONS

7200 Series Ventilator, Options, and Accessories: Operator's Manual. Nellcor Puritan Bennett, Part No. 22300 A, Sep. 1990, pp. 1-196.

(Continued)

*Primary Examiner* — Kristen Matter

(57) ABSTRACT

An exhalation valve assembly that controls the pressure of exhaled gas in a ventilation system is described. The exhalation valve assembly includes an actuator module that may be fixed to the ventilation system and a valve module, removable for cleaning or disposal, through which the exhaled gas flows and that controls the pressure and release of the exhaled gas to the environment. Other components may also be incorporated into the assembly including a filter module, a flow meter and a condensate trap.

20 Claims, 9 Drawing Sheets

U.S. PATENT DOCUMENTS

| | | |
|---|---|---|
| D300,272 S | 3/1989 | Rudolph et al. |
| D300,273 S | 3/1989 | Rudolph et al. |
| D305,165 S | 12/1989 | Rudolph et al. |
| 4,921,642 A | 5/1990 | LaTorraca |
| 4,954,799 A | 9/1990 | Kumar |
| 4,957,107 A | 9/1990 | Sipin |
| 4,991,576 A | 2/1991 | Henkin et al. |
| 4,993,269 A | 2/1991 | Guillaume et al. |
| 5,000,173 A | 3/1991 | Zalkin et al. |
| 5,020,532 A | 6/1991 | Mahoney et al. |
| 5,038,621 A | 8/1991 | Stupecky |
| 5,057,822 A | 10/1991 | Hoffman |
| 5,072,729 A | 12/1991 | DeVries |
| 5,072,737 A | 12/1991 | Goulding |
| 5,109,838 A | 5/1992 | Elam |
| 5,127,400 A | 7/1992 | DeVries et al. |
| 5,131,387 A | 7/1992 | French et al. |
| 5,134,995 A | 8/1992 | Gruenke et al. |
| 5,146,092 A | 9/1992 | Apperson et al. |
| 5,150,291 A | 9/1992 | Cummings et al. |
| 5,153,436 A | 10/1992 | Apperson et al. |
| 5,161,525 A | 11/1992 | Kimm et al. |
| 5,168,868 A | 12/1992 | Hicks |
| 5,178,155 A | 1/1993 | Mault |
| 5,237,987 A | 8/1993 | Anderson et al. |
| 5,255,675 A | 10/1993 | Kolobow |
| 5,259,373 A | 11/1993 | Gruenke et al. |
| 5,269,293 A | 12/1993 | Löser et al. |
| 5,271,389 A | 12/1993 | Isaza et al. |
| 5,277,175 A | 1/1994 | Riggs et al. |
| 5,279,549 A | 1/1994 | Ranford |
| 5,299,568 A | 4/1994 | Forare et al. |
| 5,301,667 A | 4/1994 | McGrail et al. |
| 5,301,921 A | 4/1994 | Kumar |
| 5,303,699 A | 4/1994 | Bonassa et al. |
| 5,309,901 A | 5/1994 | Beaussant |
| 5,316,009 A | 5/1994 | Yamada et al. |
| 5,319,540 A | 6/1994 | Isaza et al. |
| 5,325,861 A | 7/1994 | Goulding |
| 5,331,995 A | 7/1994 | Westfall et al. |
| 5,333,606 A | 8/1994 | Schneider et al. |
| 5,335,656 A | 8/1994 | Bowe et al. |
| 5,339,807 A | 8/1994 | Carter |
| 5,343,857 A | 9/1994 | Schneider et al. |
| 5,343,858 A | 9/1994 | Winefordner et al. |
| 5,351,522 A | 10/1994 | Lura |
| 5,355,893 A | 10/1994 | Mick et al. |
| 5,357,946 A | 10/1994 | Kee et al. |
| 5,360,000 A | 11/1994 | Carter |
| 5,368,019 A | 11/1994 | LaTorraca |
| 5,368,021 A | 11/1994 | Beard et al. |
| 5,369,277 A | 11/1994 | Knodle et al. |
| 5,383,449 A | 1/1995 | Forare et al. |
| 5,385,142 A | 1/1995 | Brady et al. |
| 5,390,666 A | 2/1995 | Kimm et al. |
| 5,398,677 A | 3/1995 | Smith |
| 5,401,135 A | 3/1995 | Stoen et al. |
| D357,532 S | 4/1995 | McCulloch |
| 5,402,796 A | 4/1995 | Packer et al. |
| 5,407,174 A | 4/1995 | Kumar |
| 5,413,110 A | 5/1995 | Cummings et al. |
| 5,438,980 A | 8/1995 | Phillips |
| 5,443,075 A | 8/1995 | Holscher |
| 5,452,714 A | 9/1995 | Anderson et al. |
| 5,467,766 A | 11/1995 | Ansite et al. |
| 5,484,270 A | 1/1996 | Adahan |
| 5,494,028 A | 2/1996 | DeVries et al. |
| 5,497,767 A | 3/1996 | Olsson et al. |
| 5,503,140 A | 4/1996 | Winefordner et al. |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power et al. |
| 5,540,220 A | 7/1996 | Gropper et al. |
| 5,542,415 A | 8/1996 | Brady |
| 5,542,416 A | 8/1996 | Chalvignac |
| 5,544,674 A | 8/1996 | Kelly |
| 5,546,935 A | 8/1996 | Champeau |
| 5,549,106 A | 8/1996 | Gruenke et al. |
| 5,568,910 A | 10/1996 | Koehler et al. |
| 5,575,283 A | 11/1996 | Sjoestrand |
| 5,596,984 A | 1/1997 | O'Mahony et al. |
| 5,598,838 A | 2/1997 | Servidio et al. |
| 5,606,968 A | 3/1997 | Mang |
| 5,616,923 A | 4/1997 | Rich et al. |
| 5,617,847 A | 4/1997 | Howe |
| 5,630,411 A | 5/1997 | Holscher |
| 5,632,270 A | 5/1997 | O'Mahony et al. |
| 5,645,048 A | 7/1997 | Brodsky et al. |
| 5,657,750 A | 8/1997 | Colman et al. |
| 5,660,171 A | 8/1997 | Kimm et al. |
| 5,662,099 A | 9/1997 | Tobia et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,678,537 A | 10/1997 | Bathe et al. |
| 5,683,232 A | 11/1997 | Adhan |
| 5,692,497 A | 12/1997 | Schnitzer et al. |
| 5,693,944 A | 12/1997 | Rich |
| 5,694,926 A | 12/1997 | DeVries et al. |
| 5,697,363 A | 12/1997 | Hart |
| 5,701,883 A | 12/1997 | Hete et al. |
| 5,701,889 A | 12/1997 | Danon |
| 5,715,812 A | 2/1998 | Deighan et al. |
| 5,762,480 A | 6/1998 | Adahan |
| 5,771,884 A | 6/1998 | Yarnall et al. |
| 5,789,660 A | 8/1998 | Kofoed et al. |
| 5,791,339 A | 8/1998 | Winter |
| 5,794,614 A | 8/1998 | Gruenke et al. |
| 5,794,986 A | 8/1998 | Gansel et al. |
| 5,797,393 A | 8/1998 | Kohl |
| 5,803,064 A | 9/1998 | Phelps et al. |
| 5,813,399 A | 9/1998 | Isaza et al. |
| 5,823,179 A | 10/1998 | Grychowski et al. |
| 5,826,575 A | 10/1998 | Lall |
| 5,829,441 A | 11/1998 | Kidd et al. |
| 5,845,636 A | 12/1998 | Gruenke et al. |
| 5,857,458 A | 1/1999 | Tham et al. |
| 5,864,938 A | 2/1999 | Gansel et al. |
| 5,865,168 A | 2/1999 | Isaza |
| 5,868,133 A | 2/1999 | DeVries et al. |
| 5,875,783 A | 3/1999 | Kullik |
| 5,876,352 A | 3/1999 | Weismann |
| 5,881,717 A | 3/1999 | Isaza |
| 5,881,722 A | 3/1999 | DeVries et al. |
| 5,881,723 A | 3/1999 | Wallace et al. |
| 5,884,623 A | 3/1999 | Winter |
| 5,906,204 A | 5/1999 | Beran et al. |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,927,274 A | 7/1999 | Servidio et al. |
| 5,927,275 A | 7/1999 | Loeser |
| 5,931,160 A | 8/1999 | Gilmore et al. |
| 5,934,274 A | 8/1999 | Merrick et al. |
| 5,937,854 A | 8/1999 | Stenzier |
| 5,937,856 A | 8/1999 | Jonasson et al. |
| 5,941,846 A | 8/1999 | Duffy et al. |
| 5,957,130 A | 9/1999 | Krahbichler et al. |
| 6,024,089 A | 2/2000 | Wallace et al. |
| 6,041,777 A | 3/2000 | Faithfull et al. |
| 6,041,780 A | 3/2000 | Richard et al. |
| 6,047,860 A | 4/2000 | Sanders |
| 6,073,630 A | 6/2000 | Adahan |
| 6,076,523 A | 6/2000 | Jones et al. |
| D429,330 S | 8/2000 | Hoenig |
| 6,095,139 A | 8/2000 | Psaros |
| 6,095,140 A | 8/2000 | Poon et al. |
| 6,099,481 A | 8/2000 | Daniels et al. |
| 6,102,038 A | 8/2000 | DeVries |
| 6,106,480 A | 8/2000 | Gama De Abreu et al. |

| | | | | | | |
|---|---|---|---|---|---|---|
| 6,116,240 | A | 9/2000 | Merrick et al. | 6,584,973 | B1 | 7/2003 | Biondi et al. |
| 6,116,242 | A | 9/2000 | Frye et al. | 6,606,994 | B1 | 8/2003 | Clark |
| 6,116,464 | A | 9/2000 | Sanders | 6,616,615 | B2 | 9/2003 | Mault |
| 6,119,686 | A | 9/2000 | Somerson et al. | 6,616,896 | B2 | 9/2003 | Labuda et al. |
| 6,123,073 | A | 9/2000 | Schlawin et al. | 6,619,289 | B1 | 9/2003 | Mashak |
| 6,123,074 | A | 9/2000 | Hete et al. | 6,622,725 | B1 | 9/2003 | Fisher et al. |
| 6,131,571 | A | 10/2000 | Lampotang et al. | 6,622,726 | B1 | 9/2003 | Du |
| 6,135,106 | A | 10/2000 | Dirks et al. | 6,629,934 | B2 | 10/2003 | Mault et al. |
| 6,135,967 | A | 10/2000 | Fiorenza et al. | 6,631,716 | B1 | 10/2003 | Robinson et al. |
| 6,142,150 | A | 11/2000 | O'Mahoney et al. | 6,644,310 | B1 | 11/2003 | Delache et al. |
| 6,148,814 | A | 11/2000 | Clemmer et al. | 6,648,831 | B2 | 11/2003 | Orr et al. |
| 6,152,132 | A | 11/2000 | Psaros | 6,648,832 | B2 | 11/2003 | Orr et al. |
| 6,152,135 | A | 11/2000 | DeVries et al. | 6,659,962 | B2 | 12/2003 | Ricciardelli |
| 6,155,986 | A | 12/2000 | Brydon et al. | 6,668,824 | B1 | 12/2003 | Isaza et al. |
| 6,158,432 | A | 12/2000 | Biondi et al. | 6,668,828 | B1 | 12/2003 | Figley et al. |
| 6,161,539 | A | 12/2000 | Winter | 6,668,829 | B2 | 12/2003 | Biondi et al. |
| 6,176,234 | B1 | 1/2001 | Salter et al. | 6,675,801 | B2 | 1/2004 | Wallace et al. |
| 6,179,784 | B1 | 1/2001 | Daniels et al. | 6,688,307 | B2 | 2/2004 | Berthon-Jones |
| 6,192,885 | B1 | 2/2001 | Jalde | 6,691,702 | B2 | 2/2004 | Appel et al. |
| 6,196,222 | B1 | 3/2001 | Heinonen et al. | 6,718,974 | B1 | 4/2004 | Moberg |
| 6,203,502 | B1 | 3/2001 | Hilgendorf et al. | 6,722,359 | B2 | 4/2004 | Chalvignac |
| 6,217,524 | B1 | 4/2001 | Orr et al. | 6,723,055 | B2 | 4/2004 | Hoffman |
| 6,220,245 | B1 | 4/2001 | Takabayashi et al. | 6,725,447 | B1 | 4/2004 | Gilman et al. |
| 6,227,196 | B1 * | 5/2001 | Jaffe et al. | 6,729,331 | B2 | 5/2004 | Kay |
| 6,269,810 | B1 * | 8/2001 | Brooker et al. .......... 128/203.12 | 6,739,334 | B2 | 5/2004 | Valeij |
| 6,269,812 | B1 | 8/2001 | Wallace et al. | 6,739,337 | B2 | 5/2004 | Isaza |
| 6,273,444 | B1 | 8/2001 | Power | 6,755,193 | B2 | 6/2004 | Berthon-Jones et al. |
| 6,283,119 | B1 | 9/2001 | Bourdon | 6,761,167 | B1 | 7/2004 | Nadjafizadeh et al. |
| 6,287,264 | B1 | 9/2001 | Hoffman | 6,761,168 | B1 | 7/2004 | Nadjafizadeh et al. |
| 6,295,330 | B1 | 9/2001 | Skog et al. | 6,763,829 | B2 | 7/2004 | Jaffe et al. |
| 6,295,985 | B1 | 10/2001 | Kock et al. | 6,772,762 | B2 | 8/2004 | Piesinger |
| 6,305,372 | B1 | 10/2001 | Servidio | 6,805,121 | B1 | 10/2004 | Flood et al. |
| 6,305,373 | B1 | 10/2001 | Wallace et al. | 6,810,876 | B2 | 11/2004 | Berthon-Jones |
| 6,306,098 | B1 | 10/2001 | Orr et al. | 6,814,074 | B1 | 11/2004 | Nadjafizadeh et al. |
| 6,308,706 | B1 | 10/2001 | Lammers et al. | 6,815,211 | B1 | 11/2004 | Blazewicz et al. |
| 6,309,360 | B1 | 10/2001 | Mault | 6,840,906 | B2 | 1/2005 | Gama De Abreu et al. |
| 6,312,389 | B1 | 11/2001 | Kofoed et al. | 6,866,040 | B1 | 3/2005 | Bourdon |
| 6,321,748 | B1 | 11/2001 | O'Mahoney | 6,877,511 | B2 | 4/2005 | DeVries et al. |
| 6,325,785 | B1 | 12/2001 | Babkes et al. | 6,886,558 | B2 | 5/2005 | Tanaka et al. |
| 6,325,978 | B1 | 12/2001 | Labuda et al. | 6,896,713 | B1 | 5/2005 | Eckerbom et al. |
| 6,349,922 | B1 | 2/2002 | Rydin | 6,908,438 | B2 | 6/2005 | Orr et al. |
| 6,357,438 | B1 | 3/2002 | Hansen | 6,938,619 | B1 | 9/2005 | Hickle |
| 6,358,215 | B1 | 3/2002 | Ricciardelli | 6,954,702 | B2 | 10/2005 | Pierry et al. |
| 6,360,745 | B1 | 3/2002 | Wallace et al. | 6,955,651 | B2 | 10/2005 | Kück et al. |
| 6,369,838 | B1 | 4/2002 | Wallace et al. | 6,960,854 | B2 | 11/2005 | Nadjafizadeh et al. |
| 6,371,113 | B1 | 4/2002 | Tobia et al. | 6,968,840 | B2 | 11/2005 | Smith et al. |
| 6,390,091 | B1 | 5/2002 | Banner et al. | 6,986,351 | B2 | 1/2006 | Figley et al. |
| 6,394,962 | B1 | 5/2002 | Gama De Abreu et al. | 6,990,980 | B2 | 1/2006 | Richey et al. |
| 6,402,697 | B1 | 6/2002 | Calkins et al. | 7,004,168 | B2 | 2/2006 | Mace et al. |
| 6,408,848 | B1 | 6/2002 | Feldman et al. | D518,172 | S | 3/2006 | Britten et al. |
| 6,412,483 | B1 | 7/2002 | Jones et al. | 7,017,574 | B2 | 3/2006 | Biondi et al. |
| 6,415,788 | B1 | 7/2002 | Clawson et al. | 7,018,340 | B2 | 3/2006 | Jaffe et al. |
| 6,419,634 | B1 | 7/2002 | Gaston, IV et al. | 7,032,589 | B2 | 4/2006 | Kerechanin, II et al. |
| 6,439,229 | B1 | 8/2002 | Du et al. | 7,036,504 | B2 | 5/2006 | Wallace et al. |
| 6,457,472 | B1 | 10/2002 | Schwartz et al. | 7,040,315 | B1 | 5/2006 | Stromberg |
| 6,463,930 | B2 | 10/2002 | Biondi et al. | 7,040,316 | B2 | 5/2006 | Connelly et al. |
| 6,467,478 | B1 | 10/2002 | Merrick et al. | 7,040,321 | B2 | 5/2006 | Göbel |
| 6,471,658 | B1 | 10/2002 | Daniels et al. | 7,043,979 | B2 | 5/2006 | Smith et al. |
| 6,484,719 | B1 | 11/2002 | Berthon-Jones | 7,066,175 | B2 | 6/2006 | Hamilton et al. |
| 6,523,537 | B1 | 2/2003 | Mas Marfany | 7,066,176 | B2 | 6/2006 | Jaffe et al. |
| 6,523,538 | B1 | 2/2003 | Wikefeldt | 7,066,177 | B2 | 6/2006 | Pittaway et al. |
| 6,526,970 | B2 | 3/2003 | DeVries et al. | 7,074,196 | B2 | 7/2006 | Kück et al. |
| 6,532,957 | B2 | 3/2003 | Berthon-Jones | 7,077,131 | B2 | 7/2006 | Hansen |
| 6,532,960 | B1 | 3/2003 | Yurko | RE39,225 | E | 8/2006 | Isaza et al. |
| 6,540,689 | B1 | 4/2003 | Orr et al. | 7,117,438 | B2 | 10/2006 | Wallace et al. |
| 6,543,449 | B1 | 4/2003 | Woodring et al. | 7,118,537 | B2 | 10/2006 | Baddour |
| 6,546,930 | B1 | 4/2003 | Emerson et al. | 7,121,277 | B2 | 10/2006 | Ström |
| 6,550,479 | B1 | 4/2003 | Duxbury | 7,128,069 | B2 | 10/2006 | Farrugia et al. |
| 6,553,991 | B1 | 4/2003 | Isaza | 7,135,001 | B2 | 11/2006 | Orr et al. |
| 6,553,992 | B1 | 4/2003 | Berthon-Jones et al. | 7,137,389 | B2 | 11/2006 | Berthon-Jones |
| 6,557,553 | B1 | 5/2003 | Borrello | 7,152,604 | B2 | 12/2006 | Hickle et al. |
| 6,557,554 | B1 | 5/2003 | Sugiura | 7,168,597 | B1 | 1/2007 | Jones et al. |
| 6,564,798 | B1 | 5/2003 | Jalde | D536,443 | S | 2/2007 | Latsos |
| 6,571,795 | B2 | 6/2003 | Bourdon | 7,183,552 | B2 | 2/2007 | Russell |
| 6,572,561 | B2 | 6/2003 | Mault | 7,195,013 | B2 | 3/2007 | Lurie |
| 6,575,163 | B1 | 6/2003 | Berthon-Jones | 7,210,478 | B2 | 5/2007 | Banner et al. |
| 6,575,164 | B1 | 6/2003 | Jaffe et al. | 7,222,623 | B2 | 5/2007 | DeVries et al. |
| 6,575,165 | B1 | 6/2003 | Cook et al. | 7,241,269 | B2 | 7/2007 | McCawley et al. |
| 6,575,918 | B2 | 6/2003 | Kline | 7,270,126 | B2 | 9/2007 | Wallace et al. |

| | | |
|---|---|---|
| 7,275,540 B2 | 10/2007 | Bolam |
| 7,291,115 B2 | 11/2007 | Cardona Burrul |
| 7,291,851 B2 | 11/2007 | DelFavero et al. |
| 7,302,949 B2 | 12/2007 | Pelerossi et al. |
| 7,320,321 B2 | 1/2008 | Pranger et al. |
| 7,334,578 B2 | 2/2008 | Biondi et al. |
| 7,335,164 B2 | 2/2008 | Mace et al. |
| 7,341,563 B2 | 3/2008 | Rich et al. |
| 7,347,205 B2 | 3/2008 | Levi |
| 7,347,825 B2 | 3/2008 | Vaughan et al. |
| 7,363,085 B1 | 4/2008 | Benser et al. |
| 7,367,337 B2 | 5/2008 | Berthon-Jones et al. |
| 7,369,757 B2 | 5/2008 | Farbarik |
| 7,370,650 B2 | 5/2008 | Nadjafizadeh et al. |
| 7,392,806 B2 | 7/2008 | Yuen et al. |
| 7,421,296 B1 | 9/2008 | Benser et al. |
| 7,427,269 B2 | 9/2008 | George et al. |
| 7,428,902 B2 | 9/2008 | Du et al. |
| 7,432,508 B2 | 10/2008 | Daniels et al. |
| 7,460,959 B2 | 12/2008 | Jafari |
| 7,475,685 B2 | 1/2009 | Dietz et al. |
| 7,484,508 B2 | 2/2009 | Younes |
| 7,487,773 B2 | 2/2009 | Li |
| 7,487,778 B2 | 2/2009 | Freitag |
| 7,500,483 B2 | 3/2009 | Colman et al. |
| 7,509,957 B2 | 3/2009 | Duquette et al. |
| 7,519,425 B2 | 4/2009 | Benser et al. |
| 7,525,663 B2 | 4/2009 | Kwok et al. |
| 7,533,670 B1 | 5/2009 | Freitag et al. |
| 7,547,285 B2 | 6/2009 | Kline |
| 7,556,038 B2 | 7/2009 | Kirby et al. |
| 7,556,042 B2 | 7/2009 | West et al. |
| 7,562,657 B2 | 7/2009 | Blanch et al. |
| 7,588,033 B2 | 9/2009 | Wondka |
| 7,610,914 B2 | 11/2009 | Bolam et al. |
| 7,617,824 B2 | 11/2009 | Doyle |
| 7,621,271 B2 | 11/2009 | Brugnoli |
| 7,634,998 B1 | 12/2009 | Fenley |
| 7,644,713 B2 | 1/2010 | Berthon-Jones |
| 7,654,802 B2 | 2/2010 | Crawford, Jr. et al. |
| 7,668,579 B2 | 2/2010 | Lynn |
| 7,686,019 B2 | 3/2010 | Weiss et al. |
| 7,694,677 B2 | 4/2010 | Tang |
| 7,699,788 B2 | 4/2010 | Kuck et al. |
| 7,717,113 B2 | 5/2010 | Andrieux |
| 7,721,735 B2 | 5/2010 | Hamilton et al. |
| 7,721,736 B2 | 5/2010 | Urias et al. |
| 7,740,591 B1 | 6/2010 | Starr et al. |
| 7,753,052 B2 | 7/2010 | Tanaka |
| 7,779,840 B2 | 8/2010 | Acker et al. |
| 7,784,461 B2 | 8/2010 | Figueiredo et al. |
| 7,810,497 B2 | 10/2010 | Pittman et al. |
| 7,814,908 B2 | 10/2010 | Psaros |
| 7,819,815 B2 | 10/2010 | Younes |
| 7,823,588 B2 | 11/2010 | Hansen |
| 7,828,741 B2 | 11/2010 | Kline et al. |
| 7,846,739 B2 | 12/2010 | von Bahr et al. |
| 7,849,854 B2 | 12/2010 | DeVries et al. |
| 7,855,716 B2 | 12/2010 | McCreary et al. |
| 7,861,716 B2 | 1/2011 | Borrello |
| 7,870,857 B2 | 1/2011 | Dhuper et al. |
| D632,796 S | 2/2011 | Ross et al. |
| D632,797 S | 2/2011 | Ross et al. |
| 7,883,471 B2 | 2/2011 | Aljuri et al. |
| 7,885,771 B2 | 2/2011 | Roecker et al. |
| 7,891,354 B2 | 2/2011 | Farbarik |
| 7,893,560 B2 | 2/2011 | Carter |
| 7,900,626 B2 | 3/2011 | Daly |
| 7,913,690 B2 | 3/2011 | Fisher et al. |
| 7,984,714 B2 | 7/2011 | Hausmann et al. |
| 7,992,557 B2 | 8/2011 | Nadjafizadeh et al. |
| 8,001,967 B2 | 8/2011 | Wallace et al. |
| 8,021,310 B2 | 9/2011 | Sanborn et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| 8,181,648 B2 | 5/2012 | Perine et al. |
| 8,210,173 B2 | 7/2012 | Vandine |
| 8,210,174 B2 | 7/2012 | Farbarik |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2001/0029339 A1 | 10/2001 | Orr et al. |
| 2001/0031928 A1 | 10/2001 | Orr et al. |
| 2002/0026941 A1 | 3/2002 | Biondi et al. |
| 2002/0082512 A1 | 6/2002 | Strom |
| 2002/0128566 A1 | 9/2002 | Gama De Abreu et al. |
| 2002/0138213 A1 | 9/2002 | Mault |
| 2002/0148468 A1 | 10/2002 | Valeij |
| 2003/0047188 A1 | 3/2003 | Mace et al. |
| 2003/0062045 A1 | 4/2003 | Woodring et al. |
| 2003/0111078 A1 | 6/2003 | Habashi et al. |
| 2003/0140921 A1 | 7/2003 | Smith et al. |
| 2003/0191405 A1 | 10/2003 | Rich et al. |
| 2004/0003814 A1 | 1/2004 | Banner et al. |
| 2004/0050387 A1 | 3/2004 | Younes |
| 2004/0087867 A1 | 5/2004 | Gama De Abreu et al. |
| 2004/0138577 A1 | 7/2004 | Kline |
| 2004/0186391 A1 | 9/2004 | Pierry et al. |
| 2004/0256560 A1 | 12/2004 | Russell |
| 2004/0261793 A1 | 12/2004 | Stromberg et al. |
| 2005/0005936 A1 | 1/2005 | Wondka |
| 2005/0034726 A1 | 2/2005 | Pittaway et al. |
| 2005/0039748 A1 | 2/2005 | Andrieux |
| 2005/0098177 A1 | 5/2005 | Haj-Yahya et al. |
| 2005/0112325 A1 | 5/2005 | Hickle |
| 2005/0124907 A1 | 6/2005 | Kuck et al. |
| 2005/0139211 A1 | 6/2005 | Alston et al. |
| 2005/0139212 A1 | 6/2005 | Bourdon |
| 2005/0150494 A1 | 7/2005 | DeVries et al. |
| 2005/0217671 A1 | 10/2005 | Fisher et al. |
| 2005/0279358 A1 | 12/2005 | Richey et al. |
| 2005/0284476 A1 | 12/2005 | Blanch et al. |
| 2005/0285055 A1 | 12/2005 | DelFavero et al. |
| 2006/0009707 A1 | 1/2006 | Daniels et al. |
| 2006/0032499 A1 | 2/2006 | Halsnes |
| 2006/0052950 A1 | 3/2006 | Pierry et al. |
| 2006/0086357 A1 | 4/2006 | Soliman et al. |
| 2006/0129054 A1 | 6/2006 | Orr et al. |
| 2006/0130839 A1 | 6/2006 | Bassovich |
| 2006/0145078 A1 | 7/2006 | Russell |
| 2006/0201507 A1 | 9/2006 | Breen |
| 2006/0241508 A1 | 10/2006 | Jaffe et al. |
| 2006/0243278 A1 | 11/2006 | Hamilton et al. |
| 2006/0249148 A1 | 11/2006 | Younes |
| 2006/0249153 A1 | 11/2006 | DeVries et al. |
| 2006/0253038 A1 | 11/2006 | Kuck et al. |
| 2006/0278223 A1 | 12/2006 | Younes |
| 2007/0000494 A1 | 1/2007 | Banner et al. |
| 2007/0017515 A1 | 1/2007 | Wallace et al. |
| 2007/0028921 A1 | 2/2007 | Banner et al. |
| 2007/0044798 A1 | 3/2007 | Levi |
| 2007/0062531 A1 | 3/2007 | Fisher et al. |
| 2007/0068518 A1 | 3/2007 | Urias et al. |
| 2007/0068530 A1 | 3/2007 | Pacey |
| 2007/0073183 A1 | 3/2007 | Kline |
| 2007/0077200 A1 | 4/2007 | Baker |
| 2007/0095347 A1 | 5/2007 | Lampotang et al. |
| 2007/0107728 A1 | 5/2007 | Ricciardelli et al. |
| 2007/0113854 A1 | 5/2007 | Mcauliffe |
| 2007/0125377 A1 | 6/2007 | Heinonen et al. |
| 2007/0142716 A1 | 6/2007 | Biondi |
| 2007/0144521 A1 | 6/2007 | DeVries et al. |
| 2007/0144523 A1 | 6/2007 | Bolam et al. |
| 2007/0149891 A1 | 6/2007 | George et al. |
| 2007/0157930 A1 | 7/2007 | Soliman et al. |
| 2007/0157931 A1 | 7/2007 | Parker et al. |
| 2007/0163579 A1 | 7/2007 | Li et al. |
| 2007/0193579 A1 | 8/2007 | Duquette et al. |
| 2007/0199566 A1 | 8/2007 | Be'eri |
| 2007/0215154 A1 | 9/2007 | Borrello |
| 2007/0221221 A1 | 9/2007 | Cooke et al. |
| 2007/0225612 A1 | 9/2007 | Mace |
| 2007/0227537 A1 | 10/2007 | Bemister et al. |
| 2007/0232952 A1 | 10/2007 | Baddour |

| | | | |
|---|---|---|---|
| 2007/0240718 A1 | 10/2007 | Daly |
| 2007/0255160 A1 | 11/2007 | Daly |
| 2007/0272241 A1 | 11/2007 | Sanborn et al. |
| 2007/0272242 A1 | 11/2007 | Sanborn et al. |
| 2007/0273887 A1 | 11/2007 | Russell |
| 2007/0282214 A1 | 12/2007 | George et al. |
| 2007/0284361 A1 | 12/2007 | Nadjafizadeh et al. |
| 2008/0000471 A1 | 1/2008 | Bolam et al. |
| 2008/0009761 A1 | 1/2008 | Acker et al. |
| 2008/0011300 A1 | 1/2008 | Andreiux |
| 2008/0021339 A1 | 1/2008 | Gabriel et al. |
| 2008/0045825 A1 | 2/2008 | Melker et al. |
| 2008/0053438 A1 | 3/2008 | DeVries et al. |
| 2008/0053441 A1 | 3/2008 | Gottlib et al. |
| 2008/0058667 A1 | 3/2008 | Pierry et al. |
| 2008/0060646 A1 | 3/2008 | Isaza |
| 2008/0060656 A1 | 3/2008 | Isaza |
| 2008/0072896 A1 | 3/2008 | Setzer et al. |
| 2008/0072902 A1 | 3/2008 | Setzer et al. |
| 2008/0078390 A1 | 4/2008 | Milne et al. |
| 2008/0083644 A1 | 4/2008 | Janbakhsh et al. |
| 2008/0091117 A1 | 4/2008 | Choncholas et al. |
| 2008/0092894 A1 | 4/2008 | Nicolazzi et al. |
| 2008/0097234 A1 | 4/2008 | Nicolazzi et al. |
| 2008/0119753 A1 | 5/2008 | Ricciardelli et al. |
| 2008/0119754 A1 | 5/2008 | Hietala |
| 2008/0135044 A1 | 6/2008 | Freitag et al. |
| 2008/0168990 A1 | 7/2008 | Cooke et al. |
| 2008/0183094 A1 | 7/2008 | Schonfuss et al. |
| 2008/0196720 A1 | 8/2008 | Kollmeyer et al. |
| 2008/0202517 A1 | 8/2008 | Mitton et al. |
| 2008/0202518 A1 | 8/2008 | Mitton et al. |
| 2008/0214947 A1 | 9/2008 | Hunt et al. |
| 2008/0230062 A1 | 9/2008 | Tham |
| 2008/0257349 A1 | 10/2008 | Hedner et al. |
| 2008/0276939 A1 | 11/2008 | Tiedje |
| 2009/0000621 A1 | 1/2009 | Haggblom et al. |
| 2009/0007914 A1 | 1/2009 | Bateman |
| 2009/0050153 A1 | 2/2009 | Brunner |
| 2009/0056708 A1 | 3/2009 | Stenzler et al. |
| 2009/0056719 A1 | 3/2009 | Newman |
| 2009/0071478 A1 | 3/2009 | Kalfon |
| 2009/0071479 A1 | 3/2009 | Nguyen et al. |
| 2009/0078251 A1 | 3/2009 | Zucchi et al. |
| 2009/0084381 A1 | 4/2009 | DeVries et al. |
| 2009/0090359 A1 | 4/2009 | Daviet et al. |
| 2009/0107500 A1 | 4/2009 | Edwards |
| 2009/0114223 A1 | 5/2009 | Bonassa |
| 2009/0133695 A1 | 5/2009 | Rao et al. |
| 2009/0137919 A1 | 5/2009 | Bar-Lavie et al. |
| 2009/0165795 A1 | 7/2009 | Nadjafizadeh et al. |
| 2009/0171176 A1 | 7/2009 | Andersohn |
| 2009/0188502 A1 | 7/2009 | Tiedje |
| 2009/0205661 A1 | 8/2009 | Stephenson et al. |
| 2009/0205663 A1 | 8/2009 | Vandine et al. |
| 2009/0217923 A1 | 9/2009 | Boehm et al. |
| 2009/0221926 A1 | 9/2009 | Younes |
| 2009/0229612 A1 | 9/2009 | Levi et al. |
| 2009/0235935 A1 | 9/2009 | Pacey |
| 2009/0241948 A1 | 10/2009 | Clancy et al. |
| 2009/0241951 A1 | 10/2009 | Jafari et al. |
| 2009/0241952 A1 | 10/2009 | Nicolazzi et al. |
| 2009/0241953 A1 | 10/2009 | Vandine et al. |
| 2009/0241955 A1 | 10/2009 | Jafari et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0241964 A1 | 10/2009 | Aljuri et al. |
| 2009/0247891 A1 | 10/2009 | Wood |
| 2009/0250054 A1 | 10/2009 | Loncar et al. |
| 2009/0250059 A1 | 10/2009 | Allum et al. |
| 2009/0255533 A1 | 10/2009 | Freitag et al. |
| 2009/0260625 A1 | 10/2009 | Wondka |
| 2009/0263279 A1 | 10/2009 | Kline et al. |
| 2009/0270752 A1 | 10/2009 | Coifman |
| 2009/0277448 A1 | 11/2009 | Ahlemn et al. |
| 2009/0293873 A1 | 12/2009 | Djupesland et al. |
| 2009/0293877 A1 | 12/2009 | Blanch et al. |
| 2009/0299430 A1 | 12/2009 | Daviet et al. |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0011307 A1 | 1/2010 | Desfossez et al. |
| 2010/0012126 A1 | 1/2010 | Gandini |
| 2010/0024820 A1 | 2/2010 | Bourdon |
| 2010/0031961 A1 | 2/2010 | Schmidt |
| 2010/0051026 A1 | 3/2010 | Graboi |
| 2010/0051029 A1 | 3/2010 | Jfari et al. |
| 2010/0059058 A1 | 3/2010 | Kuo |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0099999 A1 | 4/2010 | Hemnes et al. |
| 2010/0101577 A1 | 4/2010 | Kaestle et al. |
| 2010/0106037 A1 | 4/2010 | Kacmarek et al. |
| 2010/0125227 A1 | 5/2010 | Bird |
| 2010/0137733 A1 | 6/2010 | Wang et al. |
| 2010/0139660 A1 | 6/2010 | Adahan |
| 2010/0147302 A1 | 6/2010 | Selvarajan et al. |
| 2010/0147303 A1 | 6/2010 | Jafari et al. |
| 2010/0170512 A1 | 7/2010 | Kuypers et al. |
| 2010/0175695 A1 | 7/2010 | Jamison |
| 2010/0179392 A1 | 7/2010 | Chang et al. |
| 2010/0180897 A1 | 7/2010 | Malgouyres |
| 2010/0185112 A1 | 7/2010 | Van Kesteren et al. |
| 2010/0186744 A1 | 7/2010 | Andrieux |
| 2010/0198095 A1 | 8/2010 | Isler |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0222692 A1 | 9/2010 | McCawley et al. |
| 2010/0236553 A1 | 9/2010 | Jafari et al. |
| 2010/0236555 A1 | 9/2010 | Jafari et al. |
| 2010/0241019 A1 | 9/2010 | Varga et al. |
| 2010/0242961 A1 | 9/2010 | Mougel et al. |
| 2010/0249584 A1 | 9/2010 | Albertelli |
| 2010/0252042 A1 | 10/2010 | Kapust et al. |
| 2010/0268106 A1 | 10/2010 | Johnson et al. |
| 2010/0268131 A1 | 10/2010 | Efthimion |
| 2010/0269834 A1 | 10/2010 | Freitag et al. |
| 2010/0282258 A1 | 11/2010 | Tailor et al. |
| 2010/0286544 A1 | 11/2010 | Tanaka et al. |
| 2010/0288283 A1 | 11/2010 | Campbell et al. |
| 2010/0292601 A1 | 11/2010 | Dompeling et al. |
| 2010/0300446 A1 | 12/2010 | Nicolazzi et al. |
| 2010/0324437 A1 | 12/2010 | Freeman et al. |
| 2010/0324439 A1 | 12/2010 | Davenport |
| 2011/0004108 A1 | 1/2011 | Peyton |
| 2011/0009762 A1 | 1/2011 | Eichler et al. |
| 2011/0011400 A1 | 1/2011 | Gentner et al. |
| 2011/0023879 A1 | 2/2011 | Vandine et al. |
| 2011/0041849 A1 | 2/2011 | Chen et al. |
| 2011/0041850 A1 | 2/2011 | Vandie et al. |
| 2011/0066060 A1 | 3/2011 | von Bahr et al. |
| 2011/0126832 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0259330 A1 | 10/2011 | Jafari et al. |

FOREIGN PATENT DOCUMENTS

| | | |
|---|---|---|
| EP | 0850652 | 7/1998 |
| EP | 01205203 | 9/2004 |
| EP | 1205203 B1 | 9/2004 |
| EP | 1189649 | 6/2005 |
| EP | 0965357 | 3/2007 |
| EP | 2017586 | 1/2009 |
| FR | 2695320 | 3/1994 |
| JP | 2002136595 A | 5/2002 |

| WO | WO 9114470 | 10/1991 |
| WO | WO9611717 | 4/1996 |
| WO | WO9641571 | 12/1996 |
| WO | WO9744636 | 11/1997 |
| WO | WO 2007/102866 | 9/2007 |
| WO | WO2007109177 | 9/2007 |

OTHER PUBLICATIONS

7200 Ventilatory System: Addendum/Errata. Nellcor Puritan Bennett, Part No. 4-023576-00, Rev. A, Apr. 1988, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

Cairo et al., "Mosby's Respiratory Care Equipment, Seventh Edition", Mosby, US, XP002524651, 2004, pp. 360-361 and 775-778.

International Search Report, PCT/US2009/034363, dated Aug. 5, 2009.

International Search Report, PCT/US2009/055889, dated Nov. 26, 2009.

International Search Report, PCT/US2009/059102, dated Nov. 30, 2009.

Jaffe, Ph.D., Michael B., "Proximal Flow Measurement with the Series 3 Flow Sensors", Respironics, Inc., 2002, pp. 1-4.

PCT International Search Report Date of Mailing Mar. 3, 2011, International Application No. PCT/US2010/058265, Int'l. filing date Nov. 30, 2010, Applicant Nellcor Puritan Bennett LLC, 16 pgs.

U.S. Appl. No. 12/628,856, Notice of Allowance mailed May 23, 2012, 8 pgs.

U.S. Appl. No. 12/628,882, Office Action mailed Jul. 11, 2012, 12 pgs.

U.S. Appl. No. 12/628,905, Office Action mailed Jul. 11, 2012, 13 pgs.

U.S. Appl. No. 12/628,921, Office Action mailed Jun. 26, 2012, 10 pgs.

U.S. Appl. No. 29/360,553, Notice of Allowance mailed Oct. 13, 2011, 8 pgs.

U.S. Appl. No. 29/360,554, Notice of Allowance mailed Oct. 27, 2011, 8 pgs.

U.S. Appl. No. 29/360,554, Amendment and Response filed Jan. 6, 2012, 3 pgs.

U.S. Appl. No. 29/360,555, Notice of Allowance mailed Oct. 27, 2011, 8 pgs.

U.S. Appl. No. 12/628,856, Notice of Allowance mailed Sep. 4, 2012, 5 pgs.

U.S. Appl. No. 12/628,905, Office Action mailed Nov. 8, 2012, 13 pgs.

U.S. Appl. No. 12/628,921, Office Action mailed Sep. 21, 2012, 9 pgs.

U.S. Appl. No. 12/628,921, Advisory Action mailed Oct. 30, 2012, 2 pgs.

U.S. Appl. No. 12/628,882, Office Action mailed Nov. 14, 2012, 11 pgs.

U.S. Appl. No. 12/628,856, Notice of Allowance mailed Dec. 10, 2012, 5 pgs.

U.S. Appl. No. 12/628,905, Notice of Allowance mailed Feb. 5, 2013, 7 pgs.

U.S. Appl. No. 12/628,882, Notice of Allowance mailed Feb. 5, 2013, 3 pgs.

* cited by examiner

EXHALATION VALVE ASSEMBLY WITH INTEGRAL FLOW SENSOR

RELATED APPLICATIONS

This application is related to co-owned U.S. patent application Ser. Nos. 12/628,921; 12/628,905; 12/628,882; and 12/628,856, all filed Dec. 1, 2009, the entire disclosures of all of which are hereby incorporated herein by reference.

INTRODUCTION

Medical ventilators are designed to control the delivery of respiratory gas to a patient to supplement the patient's breathing efforts or to cause the inflation and deflation of a non-breathing patient's lung. Ventilators are often used in conjunction with a dual-limb patient circuit that conveys respiratory gas to a patient through a first tube referred to as the inspiratory limb and return exhaled gas from the patient through a second tube referred to as the expiratory limb.

In order to accurately control the delivery of respiratory gas, pressure in the patient circuit is controlled so that gas is released during an exhalation phase and, typically but not always, flow is completely blocked during an inhalation phase. However, the ventilator circuit and particularly the expiratory limb that handles the patient's exhaled gas is a challenging environment. This is true both for the control of the pressure and flow in the expiratory limb, for the monitoring that must be performed in order to accurately control the pressure and flow, and for the capture of any potentially contagious material that may be exhaled by the patient.

SUMMARY

An exhalation valve assembly that controls the pressure of exhaled gas in a ventilation system is described. The exhalation valve assembly includes an actuator module that may be fixed to the ventilation system and a removable valve module through which the exhaled gas flows and that controls the pressure and release of the exhaled gas to the environment. Other components may also be incorporated into the assembly including a filter module, a flow meter and a condensate trap.

In part, this disclosure describes an exhalation valve assembly for controlling pressure in a ventilation system. The exhalation valve assembly includes a valve module, an actuator module and a flow sensor. The valve module comprises a valve body and attached seal element, the valve body defining an inlet port providing access to a valve chamber and an exhaust port allowing gas to exit the valve chamber, the valve body having a valve seat opposite the attached seal element wherein displacement of the seal element relative to the valve seat controls gas pressure within the inlet port. The actuator module is removably connectable to the valve module and, when attached to the valve module, is operable to move the seal element relative to the valve seat to control the pressure of gas in the inlet port and the release of gas via the exhaust port. The flow sensor is contained within a flow sensor chamber in the valve body and monitors the flow of gas between the inlet port and the valve seat.

This disclosure also describes a respiratory ventilation system comprising a pressure delivery system, a inspiratory limb, an expiratory limb, a valve module, an actuator module and a flow sensor. The inspiratory limb receives respiratory gas from the pressure delivery system and delivers the respiratory gas to a patient interface. The expiratory limb that receives exhaled gas from the patient interface. The valve module comprises a valve body and attached seal element, the valve body defining an inlet port that receives the exhaled gas from the expiratory limb and directs it to through a valve seat to a valve chamber and an exhaust port allowing exhaled gas to exit the valve chamber, the valve seat opposite the attached seal element wherein displacement of the seal element relative to the valve seat controls gas pressure within the expiratory limb. The actuator module is removably connected to the valve module and, when attached to the valve module, is operable to move the seal element relative to the valve seat to control the pressure of gas in the inlet port and the release of gas via the exhaust port. The flow sensor is contained within a flow sensor chamber in the valve body and monitors the flow of gas between the inlet port and the valve seat.

The disclosure further describes a method of controlling pressure in an expiratory limb of a ventilation system. The method includes receiving a patient's exhaled gas from an expiratory limb through an inlet port into a removable valve body connected to the ventilation system, in which the removable valve body includes the inlet port, an exhalation port through which gas is released to the environment and a surface comprising a seal element. The method further includes displacing a member external to the removable valve body that interfaces with the seal element on the removable valve body, thereby changing a distance or force between the seal element and a valve seat in the removable valve body and controlling the pressure of the exhaled gas in the expiratory limb. The method also includes monitoring the flow of gas with a flow meter located between the inlet port and the valve seat of the removable housing.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of described technology and are not meant to limit the scope of the invention as claimed in any manner, which scope shall be based on the claims appended hereto.

DETAILED DESCRIPTION

This disclosure describes embodiments of exhalation valve assemblies for use in ventilators. An exhalation valve assembly controls the pressure in the ventilator patient circuit via releasing exhaled gas from the circuit. In addition, the designs are described herein that improve the serviceability of the valve assembly, the capture of exhaled liquid and the filtration of the exhaled gas. In part, this is achieved by providing a separate actuator module and a removable valve module designed to control the pressure in the ventilator circuit so that exhaled gas contacts only the removable valve module. Depending on the embodiment, a removable filter/trap module may also be provided that includes a filter and condensate trap.

Although the techniques introduced above and discussed in detail below may be implemented for a variety of medical devices, the present disclosure will discuss the implementation of these techniques in the context of a medical ventilator for use in providing ventilation support to a human patient. The reader will understand that the technology described in the context of a medical ventilator for human patients could be adapted for use with other systems such as ventilators for non-human patients and general gas transport systems in which potentially contaminated gas must be pressure-controlled and filtered before release to the atmosphere.

Medical ventilators are used to provide a breathing gas to a patient who may otherwise be unable to breathe sufficiently. In modern medical facilities, pressurized air and oxygen sources are often available from wall outlets. Accordingly, ventilators may provide pressure regulating valves (or regulators) connected to centralized sources of pressurized air and pressurized oxygen. The regulating valves function to regulate flow so that respiratory gas having a desired concentration of oxygen is supplied to the patient at desired pressures and rates. Ventilators capable of operating independently of external sources of pressurized air are also available.

Figure 1:
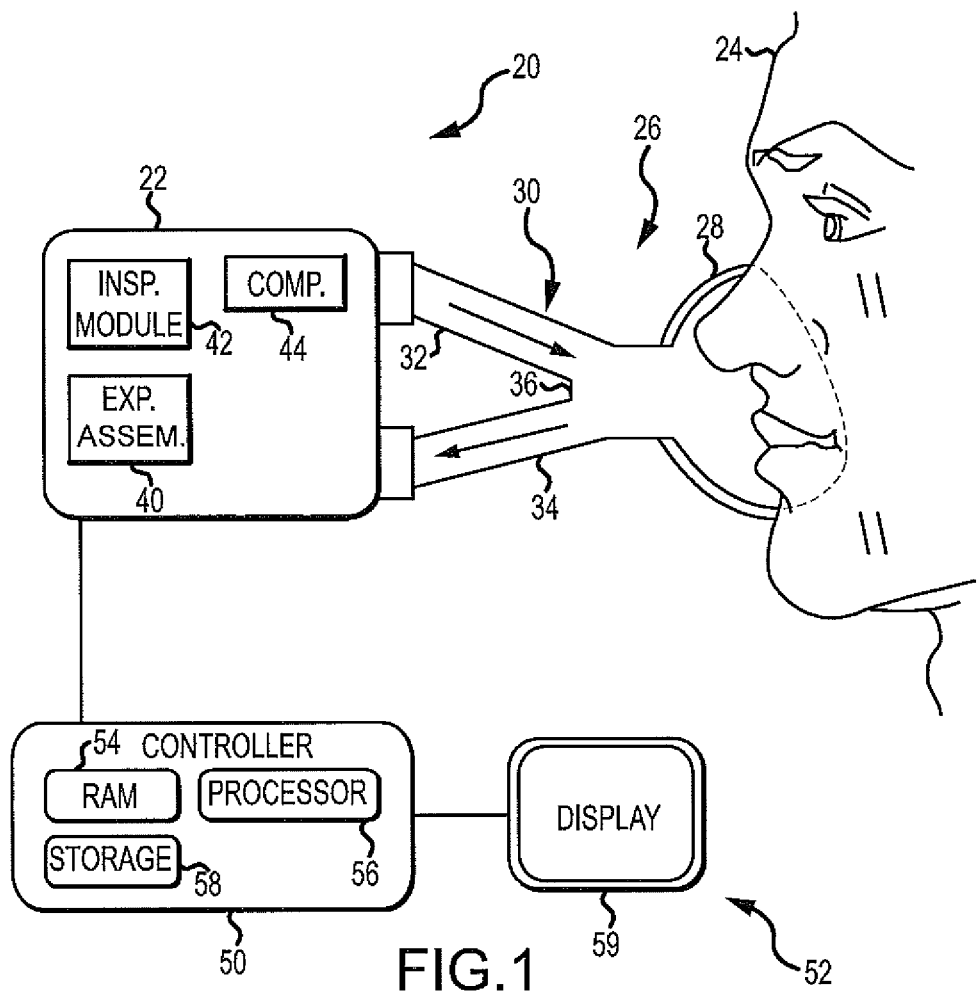
FIG. 1 illustrates an embodiment of a ventilator connected to a human patient.

FIG. 1 illustrates an embodiment of a ventilator 20 connected to a human patient 24. Ventilator 20 includes a pneumatic system 22 (also referred to as a pressure generating system 22) for circulating breathing gases to and from patient 24 via the ventilation tubing system 26, which couples the patient to the pneumatic system via physical patient interface 28 and ventilator circuit 30. Ventilator circuit 30 could be a two-limb or one-limb circuit for carrying gas to and from the patient. In a two-limb embodiment as shown, a wye fitting 36 may be provided as shown to couple the patient interface 28 to the inspiratory limb 32 and the expiratory limb 34 of the circuit 30.

The present systems and methods have proved particularly advantageous in invasive settings, such as with endotracheal tubes. However, the present description contemplates that the patient interface may be invasive or non-invasive, and of any configuration suitable for communicating a flow of breathing gas from the patient circuit to an airway of the patient. Examples of suitable patient interface devices include a nasal mask, nasal/oral mask (which is shown in FIG. 1), nasal prong, full-face mask, tracheal tube, endotracheal tube, nasal pillow, etc.

Pneumatic system 22 may be configured in a variety of ways. In the present example, system 22 includes an exhalation valve assembly 40 coupled with an expiratory limb 34 and an inspiratory module 42 coupled with an inspiratory limb 32. Compressor 44 or another source or sources of pressurized gas (e.g., pressured air and/or oxygen controlled through the use of one or more gas regulators) is coupled with inspiratory module 42 to provide a source of pressurized breathing gas for ventilatory support via inspiratory limb 32.

The pneumatic system may include a variety of other components, including sources for pressurized air and/or oxygen, mixing modules, valves, sensors, tubing, accumulators, air filters, etc. Controller 50 is operatively coupled with pneumatic system 22, signal measurement and acquisition systems, and an operator interface 52 may be provided to enable an operator to interact with the ventilator (e.g., change ventilator settings, select operational modes, view monitored parameters, etc.). Controller 50 may include memory 54, one or more processors 56, storage 58, and/or other components of the type commonly found in command and control computing devices.

The memory 54 is computer-readable storage media that stores software that is executed by the processor 56 and which controls the operation of the ventilator 20. In an embodiment, the memory 54 comprises one or more solid-state storage devices such as flash memory chips. In an alternative embodiment, the memory 54 may be mass storage connected to the processor 56 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 56. Computer-readable storage media includes volatile and non-volatile, removable and non-removable media implemented in any method or technology for storage of information such as computer-readable instructions, data structures, program modules or other data. Computer-readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the processor 56.

As described in more detail below, controller 50 issues commands to pneumatic system 22 in order to control the breathing assistance provided to the patient by the ventilator. The specific commands may be based on inputs received from patient 24, pneumatic system 22 and sensors, operator interface 52 and/or other components of the ventilator. In the depicted example, operator interface includes a display 59 that may be touch-sensitive, enabling the display to serve both as an input user interface and an output device.

Figure 2:
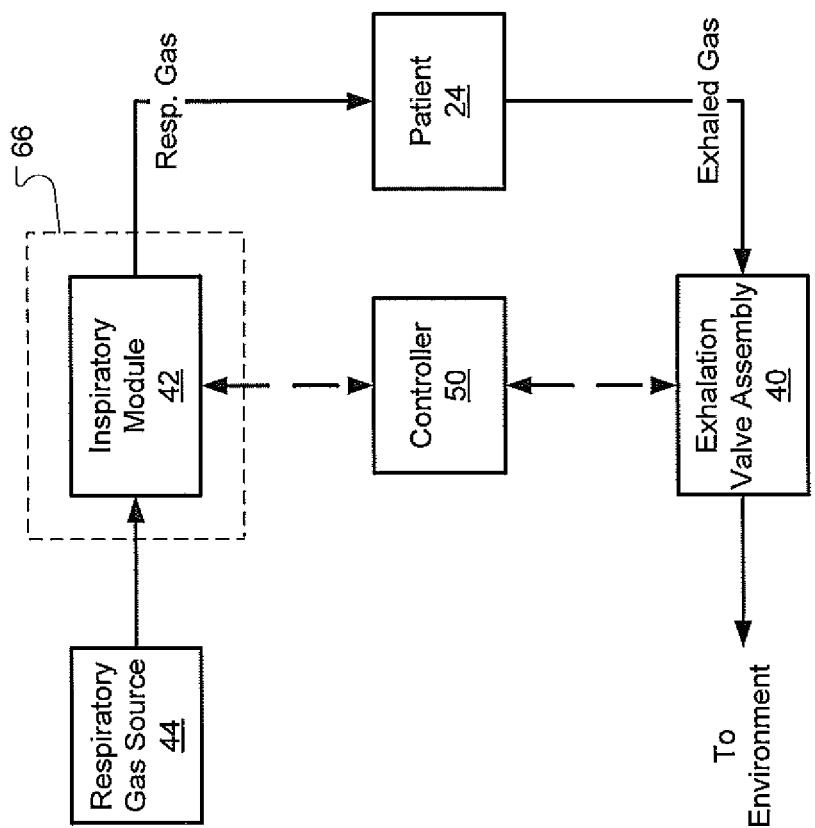
FIG. 2 schematically depicts the exemplary flow and control of gas through the system.

FIG. 2 schematically depicts the exemplary flow and control of gas through the system. As shown, controller 50 issues control commands to drive the pressure delivery system 22 (which in the embodiment shown collectively refers to the inspiratory module 42 and any equipment necessary to receive gas from the respiratory gas source 44 such as mixing manifolds, accumulators, regulators, etc.) and thereby deliver breathing gas to the patient 24 via the patient circuit. Exhaled gas is removed from the patient 24 via the expiratory limb of the patient circuit and discharged to the ambient environment through the exhalation valve assembly 40. In the embodiment shown the flow of gas through the system and the pressure of gas within the system is controlled by the controller's management of the delivery of gas through the inspiratory module 42 and the pressure in the circuit via the controller's management of the release of gas by the exhalation valve module 50.

Figure 3:
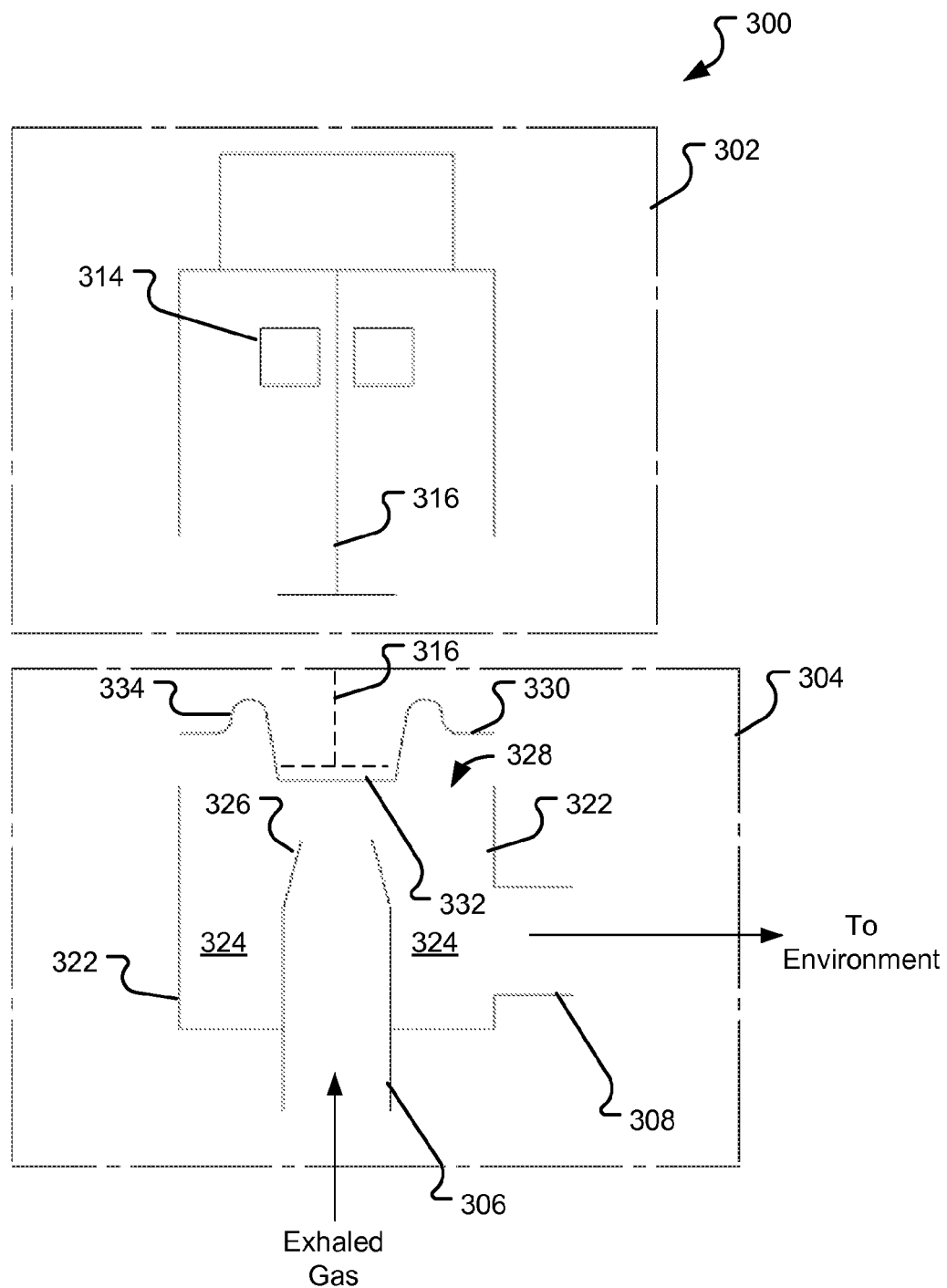
FIG. 3 illustrates an embodiment of an exhalation valve assembly having a removable valve module.

FIG. 3 illustrates an embodiment of an exhalation valve assembly. The exhalation valve assembly 300 is illustrated in a sectional, exploded view to conceptually show the different components of the assembly and how they operate relative to each other. The exhalation valve assembly 300 shown can be considered as having two distinct elements: an actuator module 302 that is a fixed part of the ventilator (not shown) and a removable valve module 304. The valve module 304 receives exhaled gas from a patient through an inlet port 306 and discharges it to the ambient atmosphere via an exhaust port 308. As described below, the actuator module 302 physically interfaces with the valve module 304 to control the pressure of gas in the inlet port 306 of the valve module 304 by changing the position of a valve seal 332 in the valve module 304 with respect to a valve seat 326. By controlling the pressure in the inlet port 306 the actuator module 302 also affects the flow of gas through the valve module 304. The designs are such that the removable valve module 304 contains all components that are exposed to the exhaled gas from the patient. In this way, cleaning the exhalation assembly requires only replacement or cleaning of the used exhalation valve module 304.

In the embodiment shown, the actuator module 302 is incorporated into the ventilator and includes a drive element 314 that displaces a member 316, such as a poppet or shaft. As shown, the drive element 314 is a linear motor, such as a voice coil motor, that drives a poppet 316. Alternative drive elements 314 include piloted pressure chambers, stepper motors, solenoids or any device capable of displacing a member or surface or applying a force on a member or surface. Although the term displacement is primarily used herein, one of skill in the art will recognize that the pressure is regulated primarily from the application of force to the seal element. The term displacement is used as shorthand for this process. Likewise, the poppet 316 may be replaced by a shaft, pin, or surface that can be displaced from the actuator module 302.

The actuator module 302 also includes an attachment portion or mechanism (not shown) that interfaces with the valve module 304 allowing the valve module 304 to be removably attached to the actuator module 302. The attachment portion includes one or more connector elements that mate with complementary elements on the valve module 304. Examples of connector elements include latches, levers, clasps, spring loaded elements, threads for screw mounting, or snaps and any suitable attachment technique, now known or later developed, may be used. The attachment portion allows the valve module 304 to be installed in a way that the poppet 316 is positioned adjacent to a moveable seal 332 on the valve module 304 (illustrated in FIG. 3 by poppet 316 in dashed lines). The attachment portion may also be designed to prevent the valve module 304 from being connected to the actuator module 302 in any non-operable configuration.

In the embodiment shown, the valve module 304 includes a valve body 322 and a valve seal with integrated diaphragm (the valve seal with integrated diaphragm will be referred to collectively as the seal element 330 and will be discussed in greater detail below).

The valve body 322 may be a unitary body of any suitable material such as plastic, aluminum, stainless steel, etc., however, because under certain conditions the valve module 304 may be treated as a disposable component, expensive materials are not preferred. In the embodiment illustrated in FIG. 3, the valve body 322 partially defines an interior volume referred to generally as the valve chamber 324. The valve body 322 also includes an inlet port 306 and an exhaust port 308, both of which provide access to the valve chamber 324. In the embodiment shown, the inlet port 306 provides access to the valve chamber 324 through the valve seat 326. In an alternative embodiment (not shown), the valve seat 326 is located at the exhaust port 308 instead of the inlet port 306.

The valve body 322 also provides access to the valve chamber 324 through a seal/diaphragm orifice 328. The edge of the seal/diaphragm orifice 328 may be provided with one or more retainers such as lips, ridges or ribs so that the seal element 330 can be removably attached. When attached, the seal element 330 and the valve body 322 form a substantially airtight seal so that the inlet port 306 and the exhaust port 308 are the only routes for gas to enter the valve chamber 324. In an alternative embodiment, the seal element 330 may be irremovably attached to the valve body 322, for example the two components may be bonded together by adhesive or in some other manner.

The seal element 330, as mentioned above, comprises a valve seal 332 portion and integral flexible diaphragm 334 portion. In an embodiment, the seal element 330 is a unitary construction of molded, flexible material such as silicon rubber. Preferably, the material is flexible and resists wear and degradation. Although silicon rubber is preferred due to its resistance to degradation over time and other properties, less desirable materials such as viton rubber, elastomers or similar may be used. Alternatively, the seal element 330 may be made from a flexible diaphragm made out of a first material bonded to a valve seal 332 made from a second material having different properties. In yet another embodiment, the seal 332 or the diaphragm 334 may be coated on one or both sides with compounds that reduce the gas transport through the seal element 330 or improve the performance of the valve seal 332, such as by improving its interface with the valve seat 326.

When molded as a unitary construction, the diaphragm 334 and the valve seal 332 portions of the seal element 330 may be provided with different shapes, thicknesses or surfaces in order to improve the performance of the seal element 330. For example, the diaphragm 334 may be shaped to improve the flexibility of the diaphragm 334 by providing curved sections as shown. Likewise, the seal 332 may be molded with a relatively thicker cross section having a surface shaped to be the compliment of the valve seat 326. Any suitable design for the seal element 330 may be used as long as the seal element 330 can be effectively displaced by the actuator module 302 to control the pressure in the inlet port 306.

In a ventilator embodiment, the inlet port 306 is attached to and received exhaled gas from the expiratory limb of the ventilation system. As may be appreciated from the discussion above, the valve module 304 creates a flow path through the inlet port 306 into the valve chamber 324 and out through the exhaust valve 308 to the atmosphere. The flow path goes through the valve seat 326 opposed by the valve seal 332. The relative position of the poppet 316 to the valve seat 326 is changed in order to control the pressure in the inlet port 306. Depending on the embodiment, the valve seat 326 may be located at the entrance of the inlet valve (as shown) into the valve chamber 324 or at some other location along the flow path. Due to the separation of the actuator module 302 from contact with exhaled gas by the seal element 330, any contamination due to contact with exhaled gas is limited to the internal surfaces of the valve module 306.

Figure 4:
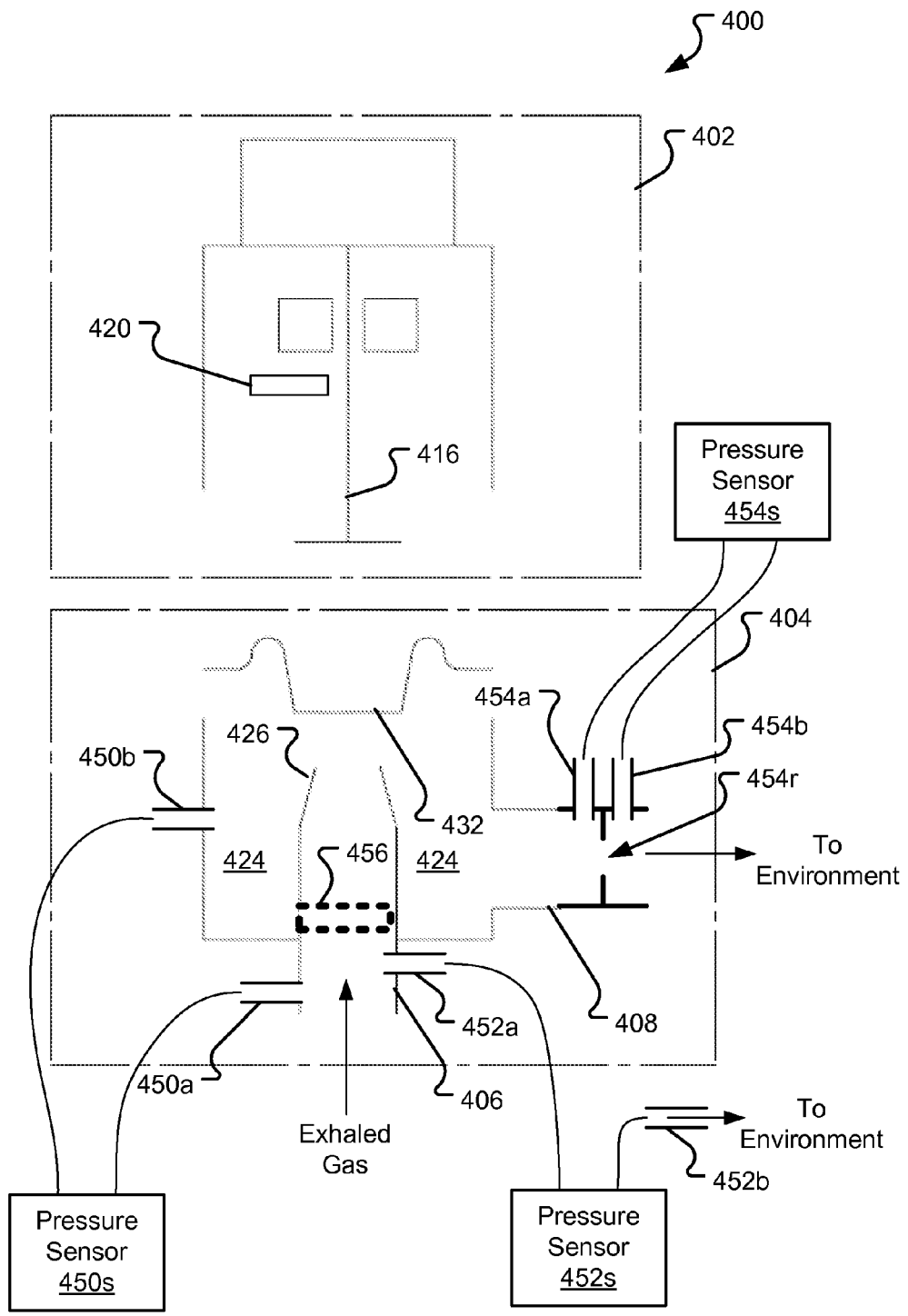
FIG. 4 illustrates another embodiment of an exhalation valve assembly having an exhalation valve module with incorporated pressure and/or flow sensors.

FIG. 4 illustrates an embodiment of an exhalation valve assembly with an integrated pressure and/or flow sensing capability. Again, the exhalation valve assembly 400 shown can be considered as having two distinct elements, an actuator module 402 and a removable valve module 404. In the embodiment shown, in addition to controlling the pressure of gas in the inlet port of the valve module 404 and isolating exhaled gas in the removable valve module 404, the exhalation valve assembly 400 includes one or more sensors 450, 452, 454, 456 that report data to the ventilator. With the exception of the sensors described below, the actuator module 402 and valve module 404 are as described above with reference to FIG. 3.

FIG. 4 illustrates several different flow and pressure sensor configurations which could be implemented separately and independently or in any combination. The data from any or all of these configurations could be used by ventilation system in the delivery of respiratory gas to the patient. For example, one or more of the sensors described above could be used to provide the expiratory limb flow or pressure data necessary to delivery respiratory to the patient.

A first sensor configuration is a flow sensor 450 in the form of a differential pressure sensor that comprises a pressure sensor 450s connected to two pressure taps 450a and 450b providing access to different points in the flow path through the valve module 404. One tap 450a provides access to the flow path on the inlet side of the valve seat 426, illustrated as a pressure tap into the valve module inlet port 406. The other tap 450b provides access to the flow path on the exhaust side of the valve seat 426, illustrated as a pressure tap into the valve chamber 424 although it could also be located in the exhaust port 408. Depending on the exact location of the valve seat 426 relative to the inlet and exhaust ports, either of the taps could be located to provide access to the valve chamber 424. As is known in the art, flow can be determined by measuring the differential pressure across a known flow restriction under known conditions of temperature and gas characteristics. In this configuration, the restriction is provided by the orifice between the valve seat 426 and the seal 432. Although this orifice is variable, it can be determined at any time through the use of a position sensor 420 in the actuator module 402. In this configuration, the position of the poppet 416 is correlated with an orifice size so that if the position is known, the resulting orifice size is known. Such a correlation may be predetermined by the manufacturer or periodically determined calibrated under conditions of known flow, such as during a ventilator startup routine. Other information necessary to the determination of flow using the flow sensor 450 (e.g., temperature, gas density, etc.) may be obtained in real time from the ventilation system's monitoring of the patient circuit or may be assumed.

In another sensor configuration a flow sensor 452 is provided in the form of a differential pressure sensor that comprises a pressure sensor 452s connected to a pressure tap 452a providing access to the flow path on the inlet side of the valve seat 426, illustrated as a pressure tap into the inlet port 406. Instead of providing a second tap into the valve module 404, the pressure sensor 452s uses the ambient atmospheric pressure obtained from any location near the ventilator. In this configuration, one simple embodiment is to provide a tap 452b to the atmosphere at some point near the pressure sensor 450s. In this configuration like the previous one described, the restriction is provided by the orifice between the valve seat 426 and the seal 432 and otherwise operates in a similar fashion.

In yet another sensor configuration a flow sensor 454 is provided in the form of a differential pressure sensor that comprises a pressure sensor 454s connected to two pressure taps 454a and 454b providing access to either side of a fixed restriction 454r in the flow path. The pressure taps 454a, 454b and flow restriction 454r may be located anywhere in the flow path in the valve module 404. FIG. 4 illustrates the pressure taps 454a, 454b and flow restriction 454r as being located in the exhaust port. The flow sensor 454 (that is pressure taps on either side of a known flow restriction) corresponds to a standard design and is well known in the art.

In yet another configuration, a flow meter such as a hot wire anemometer flow meter 456 is provided at some location in the flow path through the valve module 404. Although any flow meter may be used, hot-wire anemometers flow meters have the advantages of being small and having no moving parts. Hot wire anemometer-based flow meters are known in the art, and such flow meters may measure flow based on the cooling of a heated wire or based on the current required to maintain a wire at a fixed temperature when the wire is exposed to the flow of gas. In the embodiment shown, the flow meter 456 is located in the inlet port 406 at the base of the valve seat 426. Although a hot wire anemometer-based flow meter is described, any suitable flow meter now known or later developed may be used.

Any combination of the configurations described above may also be used. For example, in a preferred embodiment a pressure sensor, such as the pressure sensor 452s connected to a pressure tap 452a providing access to the flow path on the inlet side of the valve seat 426 and which the pressure sensor 452s uses the ambient atmospheric pressure obtained from any location near the ventilator, and a flow meter 456 are both provided. Using the information concerning the known distance between the valve seat and the seal element, the pressure sensor 452s data can be used to calculate a second estimate of the flow of gas through the valve module at any given time. Such a calculation may involve performing actual mathematical computations or may simply involve correlating a measured pressure drop and an indicator of the distance between the valve seat and the seal element using a predetermined look-up table describing a known relationship between the flow, differential pressure and seal element location. The two flow values, that measured directly using the flow meter 456 and that calculated from the pressure differential, can then be compared in order to make assessments as to the different aspects of the ventilation system and to provide better control of the gas delivery to the patient. For example, the ventilation system may perform one or more actions related to the delivery of gas to the patient based on the comparison of the two flow values. Such actions may include transmitting an alarm or notification regarding the performance of either the flow meter 456 or the pressure sensor 452s; using a flow value derived from two flow values, e.g., an average of the two, to change the pressure or flow of gas being delivered to the patient.

Figure 5:
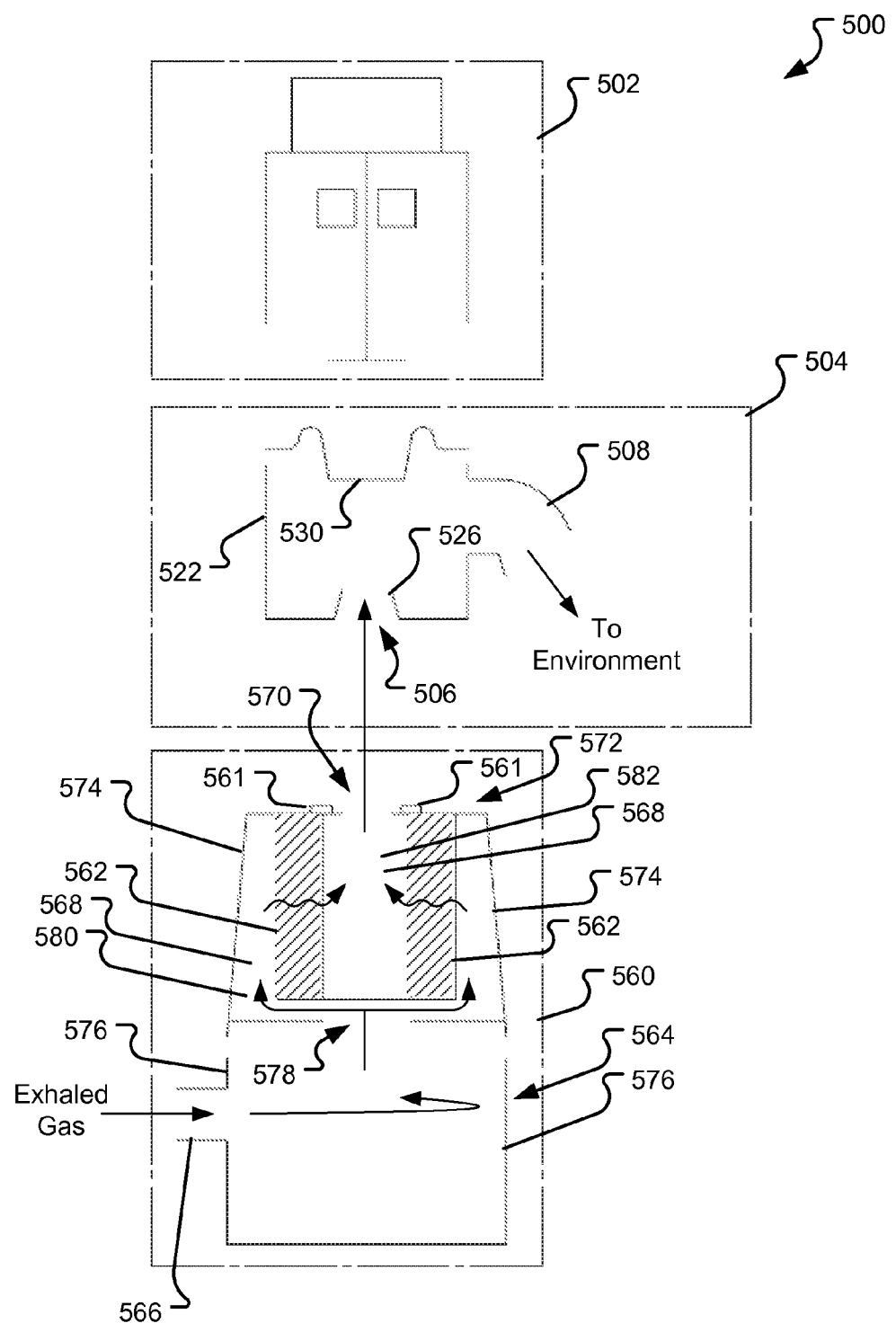
FIG. 5 illustrates yet another embodiment of an exhalation valve assembly having an exhalation valve module with incorporated filter and condensation trap.
Figure 6:
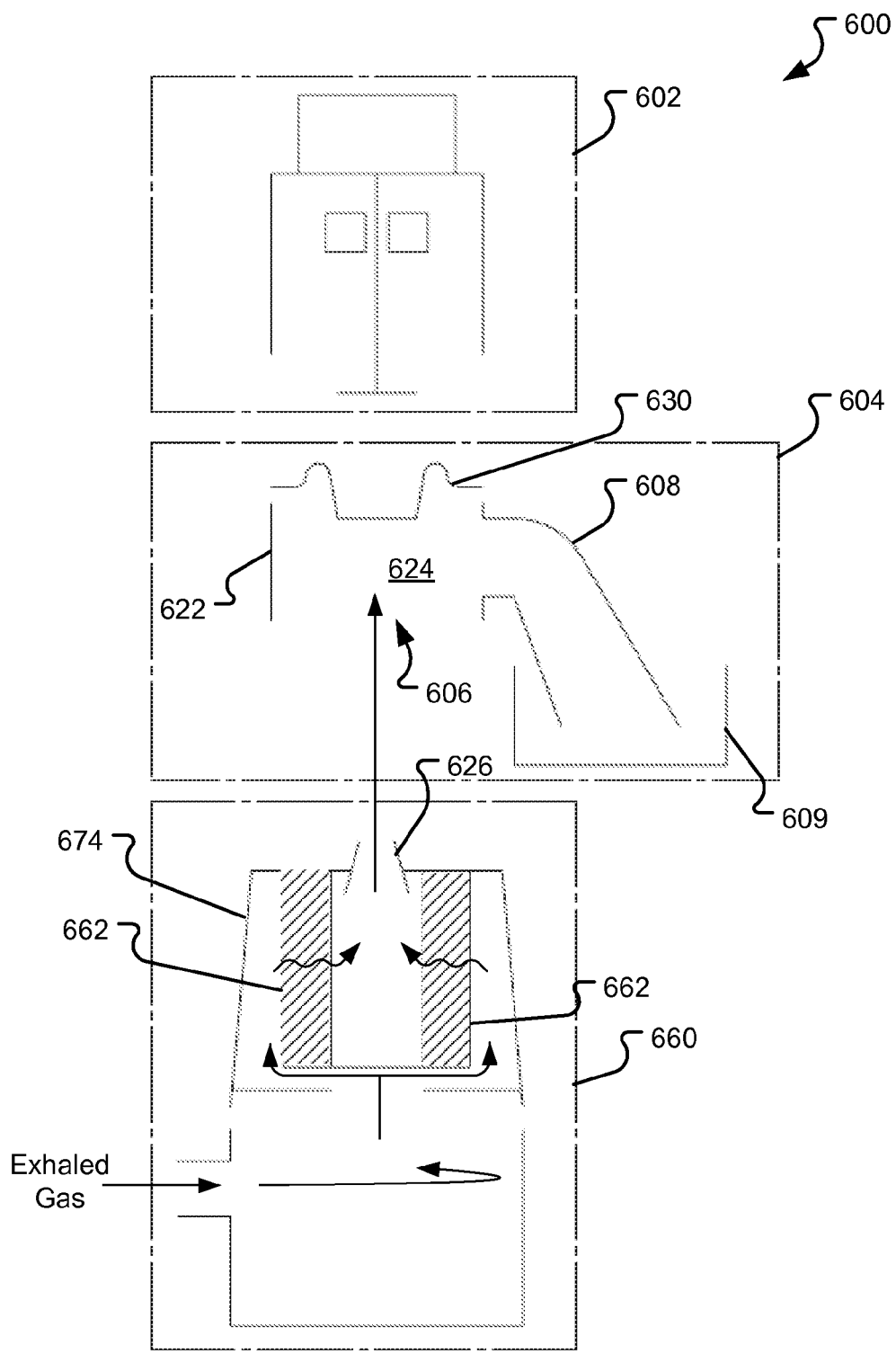
FIG. 6 illustrates a second embodiment of an exhalation valve assembly having an exhalation valve module with incorporated filter and condensation trap.

FIGS. 5-6 illustrate alternate embodiments of an exhalation valve assembly with a valve module and a filter and condensation trap. For the sake of discussion the assembly shown in FIG. 5 can be considered to have three elements: an actuator module 502 and a valve module 504 such as those described above; and a filter/trap module 560. The filter/trap module 560 introduces a filter 562 and condensate trap 564 into the flow path prior to exhaled gas entering the valve module 504. The filter/trap module 560 connects to valve module 504 and may be independently removable from the valve module 504 in order to allow for easy disposal of the enclosed filter media and any condensation captured in the trap. As discussed in greater detail below with reference to FIG. 7, the filter/trap module 560 may also be removed from the ventilator by removing the valve module 504 with the filter/trap module 560 attached, thus removing all components of the exhalation assembly that were in contact with exhaled gas.

FIG. 5 illustrates an embodiment of an exhalation valve assembly with a valve module and a filter and condensation trap in which the actuator module 502 and the valve module 504 are as described above with reference to either FIG. 3 or 4. The valve module 504 includes an attachment surface or mechanism (not shown) allowing the filter/trap module 560 to be attached. As described above, the attachment surface may incorporate any suitable attachment means for attaching the two modules. For example, any attachment surface may incorporate a seal, such as an O-ring or other sealing device 561, in order to provide a greater level of airtight fit when components are attached.

In the embodiment shown, the filter/trap module 560 can be considered as two distinct components, a filter component 572 that includes a filter body 574 enclosing a volume referred to as the filter chamber 568 that contains the filter 562; and a condensate trap component 564 that consists primarily of a trap body 576 formed to act as a condensate trap. The two components 572, 564 may be a unitary body or may be two separate bodies that are removably connected (e.g., the trap 564 can be unscrewed or unclipped from the filter body 574) as shown in the exploded view in FIG. 5. As described above, the bodies of the two components may be made of any suitable material. In an embodiment, transparent plastic is used so that the level of condensate in the trap 564 and the condition of the filter 562 can be visually inspected. Alternatively one or more transparent windows in an opaque material may be provided for visual inspection. As discussed in greater detail below, it is beneficial to independently control the temperature of the two components and the selection of body materials may be made to facilitate or inhibit heat transfer depending on the embodiment.

The filter/trap module 560 alters the flow path of the exhaled gas prior to entering the valve module 504. Exhaled gas is received from the expiratory limb of the ventilation system and enters the filter/trap module 560 at the trap inlet port 566. After a residence time in the condensate trap 564, exhaled gas flows into the filter chamber 568 and through the filter 562 (diffusion through the filter being illustrated by wavy airflow lines). Filtered gas then flows through the filter exhaust port 570 into the valve module inlet port 506.

Turning now to the condensate trap 564, in an embodiment the condensate trap 564 consists essentially of the trap body 576 enclosing a volume referred to as the condensate chamber. In an embodiment, the volume of the condensate chamber may be selected in order to provide a specific residence time under average flow conditions, noting that the residence time of the condensate chamber is equivalent to its volume divided by the flow rate of gas. The residence time may be selected based on the heat transfer characteristics of the materials and configuration of the modules in order to provide sufficient time for moisture in the exhaled gas to condense out of the gas stream. The trap body 576 also includes a trap inlet port 566 to which an expiratory limb (not shown) can be attached to receive exhaled gas and an attachment portion for attaching the trap body 576 to the filter body 574. In the embodiment shown, the trap body 576 is roughly cup-shaped with the attachment portion at the opening of the cup. The trap body 576 attaches to the filter body 574 so that the opening of the cup-shaped body is covered by the filter body 574 and encloses the condensate chamber.

In an embodiment, the condensate trap 564 may be provided with a manifold, diffuser, fin or other passive flow control element that directs the flow of the exhaled gas entering the condensation chamber. One purpose of this is to promote the cooling of the exhaled gas to facilitate condensation of any moisture exhaled by the patient. Improved cooling results in relatively more condensate getting caught in the trap 564 which improves the performance of the filter 562 and the other downstream components.

For example, in an embodiment the trap inlet port 566 may be located and oriented in an off-center configuration so that gas flow enters flowing in a direction that is tangential against an interior wall of the condensate trap body 576, thereby creating a flow along the interior surface of the trap body 576 without redirecting the incoming flow using a flow control element. Alternatively, the inlet trap inlet port 566 could be configured so that gas flow enters the condensate chamber and is redirected by fin or other flow control element to travel along a wall of the condensation chamber. Both embodiments have the effect of creating a vortex flow in the condensate chamber and along interior wall's surface, thereby increasing the heat transfer between the walls of the trap body and the incoming gas. However, use of flow control element may increase the resistance of the assembly 500 to flow, which may not be preferred. Additional passive flow control elements such as fins that direct the flow in a spiral pattern around the condensation chamber before the flow exits into the filter body 574 may be provided.

Additional modifications may be made to facilitate the cooling of the condensate trap 564. For example, in the embodiment shown the condensate trap 564 when attached to the ventilator is exposed to the ambient atmosphere. As most medical environments are maintained at a relatively cool temperature, this serves to cool the condensate trap 564. In another embodiment, a circulation fan on the ventilator may be provided that directs a flow of cool air onto the condensate trap 564. In yet another embodiment, a cooling element such as a chilled surface may be provided on the ventilator that contacts the condensate trap 564 when the trap is installed. Other methods for cooling the condensation chamber will be immediately suggested to one skilled in the art and any such method may be employed.

In an embodiment the condensate trap 564 may be provided with a drain for the removal of any condensate that may be collected. Alternatively, removal of condensate may be accomplished by removing the trap body 576 and either replacing it with a new body 576 or emptying the condensate from it before reattaching it. In yet another embodiment, it may be desirable to prevent removal of the condensate during ventilation, in which case the trap body 576 may be fixed or integral with the filter body 574 so that the only way to remove the condensate is to remove and replace the filter/trap module as a unit. In yet another embodiment, the condensate may be drained from the filter body 574 through a drain port (not shown).

The filter chamber 568 contains the filter 562 which effectively divides the chamber 568 into two volumes: a first volume 580 that receives the unfiltered gas from the condensate trap and a second volume 582 that collects the filtered gas. In the embodiment shown, a hollow cylindrical filter 562 is illustrated and unfiltered gas is filtered by passing the gas from the exterior 580 of the filter chamber into the annulus 582 at the center of the filter 562. The top and bottom of the cylindrical filter 562 are sealed to the interior surface of the filter chamber 568 to prevent unfiltered gas from getting into the annulus 582. Other filter configurations are also possible and any suitable filter shape or configuration could be used so long as it is contained with a filter body 574 and filters the gas leaving condensate trap 564 prior to delivering it to the valve inlet port 506.

The filter component 572 includes a filter inlet port 578 provided in the filter body so that when the filter body 574 and condensate trap body 576 are attached, cooled gas can enter the filter component from the condensation chamber. In the embodiment shown, the filter inlet port 578 is located within the portion of the filter body that covers the opening of the condensate trap body to enclose the condensate chamber. Other configurations are possible.

The filter inlet port 578 directs the exhaled gas from the condensate chamber to the first volume 580 in the filter chamber 568. This may be facilitated by the use of a manifold or other passive flow distribution mechanism in order to evenly distribute the gas to be filtered along the surface of the filter 562. After gas has passed through the filter 562 it enters the second volume 582 of the filter chamber and then exits via the filter exhaust port 570 into the valve module 504.

In an embodiment, the filter body 574 is detachable from both the valve module 504 and the condensate trap 564 and the body 574 is provided with the necessary attachment mechanisms to facilitate this. Again, any specific attachment mechanism or technique may be utilized.

When attached to the valve module 502, the filter chamber 568 is fully enclosed by the valve body 522 and the filter body 574 such that the only flow paths into or out of the filter body 574 are the filter inlet port and the filter exhaust port. In the embodiment shown in FIG. 5, the filter body 574 is substantially cup-shaped in which the bottom of the cup is shaped to sealingly engage one end of the tubular filter 562. The other end of the filter 562 is adapted to engage an exterior surface of the valve body 522 such that detachment of the filter body 574 from the valve body 522 allows the filter 562 to be accessed and removed/replaced. In this embodiment, the filter exhaust port may be formed by the annulus of the filter 562 which is exposed to the valve inlet port 506. Depending on the embodiment, the valve inlet port 506 may be provided with a protruding nipple or tube (not shown) for guiding the attachment of the filter body 574 to the valve body 522 and providing a better seal between the valve body and the filter. The valve inlet port 506 may also be designed to provide flow shaping and pre-conditioning, such as to prepare the flow for measurement.

In an alternative embodiment, a removable cap (not shown) may be provided that attaches to the filter body 574 in order to enclose the filter 562 into the filter chamber 568. The cap may be provided with a hole or aperture as the filter exhaust port that when installed is positioned on the valve inlet port.

It may be preferred to maintain the filter chamber 568 at a temperature greater than that of the condensate trap to inhibit any further condensation within the exhalation assembly 500. In an embodiment the filter component 572 may be provided with active heating or passive insulation. For example, in an embodiment a heating element may be located in or near the filter body. In yet another embodiment, the filter body and ventilator housing may be designed to create a substantially enclosed volume of insulating air around the filter body or the portion of the filter body containing the filter chamber. To effect this, the filter body 574 may be provided with a partial secondary wall or integrated cover that complements the shape of the ventilator housing around the filter body when it is installed so that a substantially trapped air space is created around the filter chamber (See FIGS. 8-9 for an illustration of an embodiment of a cover). Alternatively, a movable cover could be provided on the ventilator housing that encloses a chamber in the ventilator housing within which the filter body resides when installed. Such designs need not be airtight to serve to create an insulating layer of air around the walls of the filter chamber 568 that is relatively unaffected by the movement ambient air outside of the cover and ventilator housing.

In yet another embodiment, such a trapped air space around the filter body could be actively heated, such as by passing waste heat from the electronics in the ventilator through the insulating volume or to a heat sink exposed to the insulating volume or by blowing heated air into the trapped air space. Other ways of heating the filter chamber will be immediately suggested to one of skill in the art and any such heating methods may be used. It should be observed that because of the vertical configuration of the exhalation assembly with the condensate trap at the bottom, adding heat (or passively preventing heat from being released to the ambient atmosphere) serves to reduce any condensation in the modules above the condensate trap without interfering with the operation of the condensate trap.

In an embodiment (not shown), one or more sensors or pressure taps may be incorporated into or near the filter/trap module 560. For example, pressure taps as described in FIG. 4 located on the inlet side of the valve seat 526 can be located within the flow In the embodiment shown, the modules are vertically oriented with the actuator module 502 on top, the valve module 504 below the actuator module 502 and the filter component 572 below the valve module and the condensate trap component 564 below that. This orientation is efficacious for several reasons. One reason is that the seal element 530 in the valve module 504 can act as a check valve in cases where there is a sudden drop in the expiratory limb pressure. Another reason is that the condensate will naturally pool in the trap body due to gravity. Yet another reason is that since heat rises, maintaining the condensate trap 564 as the lowest component allows for a beneficial heat profile through the exhalation valve assembly 500.

FIG. 6 illustrates yet another embodiment of an exhalation valve assembly in which the valve seat is a component of the filter/trap module rather than being built into the valve module. In the embodiment shown the actuator module 602, the valve module 604 and the filter/trap module 660 are substantially as described above with the exception of the valve seat 626. Rather than having the valve seat 626 as a component of the valve module 604, the valve seat is built into a top portion of the filter/trap module 660 that when attached it places the valve seat 626 in its position opposite the seal element 630. In this embodiment, the valve body 622 may be provided with a floor having an inlet port 606 through which the valve seat 626 penetrates when the filter/trap module 660 is installed. Alternatively, the valve body 622 could be substantially open so that when installed the surface of the filter/trap module 660 around the valve seat 626 forms one of the walls defining the valve chamber 624 as shown.

In the embodiment shown in FIG. 6, the valve module 604 is illustrated as having an outlet port 608 in a hood configuration. The outlet port 608 directs the flow the generally downward into a second condensate trap 609 attached below the outlet port 608 to catch any secondary condensate that may occur when the exhaust gas exiting the valve module 604 is cooled to the ambient temperature.

In either embodiment, with relation to monitoring devices, the filter/trap module 660 may be modified as described above to include one or more pressure taps or flow sensors such as hot wire sensors. For example, a hot wire flow sensor could be provided between the valve seat 626 and the top of the filter 662 such as being built into the top of the filter/trap module 660.

In the embodiment of FIG. 6, if the entire filter body is not be considered disposable, then access may be effected to the filter 662 by providing a filter body 674 that can be taken apart. One possible design is providing a removable top (not shown) to the filter body 674 that includes the valve seat 626 and that when separated from the rest of the filter body 674 allows the filter 662 to be removed. Such a removable top may further be provided with the sensor elements, if any, allowing the expensive monitoring components to be cleaned and placed back into service easily by simply sanitizing the removable top.

The above describes but only a few possible designs of a valve seat integrated into a filter module. Other methods of mechanically incorporating the valve seat into the filter or combined filter and trap module rather than the valve module are possible and any such design may be used.

Figure 7:
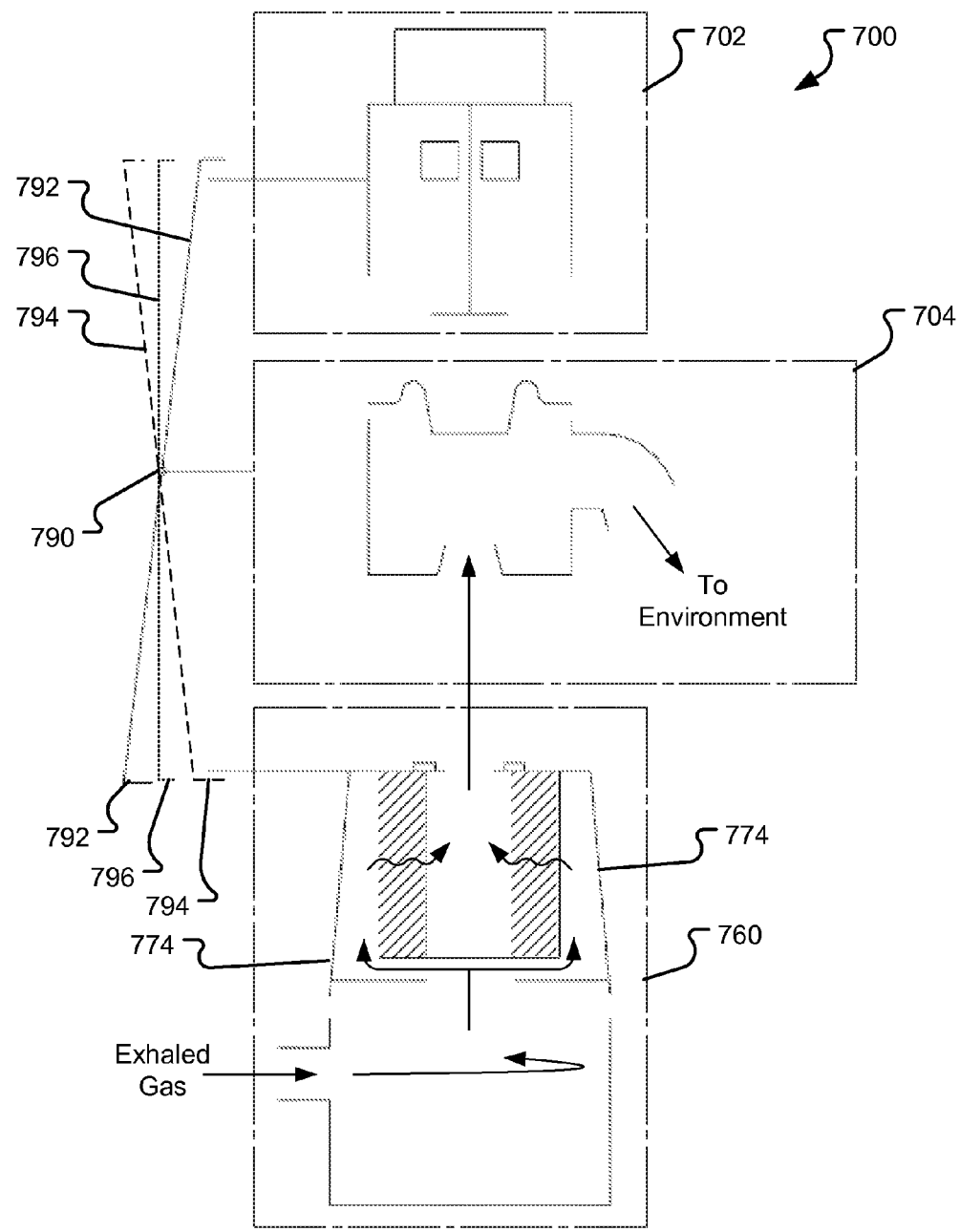
FIG. 7 illustrates a locking mechanism that switches between a contagious and non-contagious patient configuration.

FIG. 7 illustrates an embodiment of a contamination control switch for use with an exhalation valve assembly. For the purposes of illustrating the latch 790, an exhalation valve assembly 700 corresponding to that shown in FIG. 5 illustrated. That is, the exhalation valve assembly includes three main components an actuator module 702 fixed to the ventilator, a valve module 704 and a filter/trap module 760.

One purpose of the contamination control latch 790 is to prevent reuse of and ensure the cleaning or disposal of the valve module 704 and filter/trap module 760 after they has been used with a patient considered to be contagious by the treating health professionals. The contamination control latch 790 is illustrated conceptually in FIG. 7 as a two position latch attached to the valve body 774 that selectively engages either the actuator module 702 or the filter/trap module 760.

In a first, non-contagious patient position 792, the contamination control latch 790 fixes the valve module 704 to the actuator module 702 so that the filter/trap module 760 can be freely removed. This prevents the accidental removal of the valve module 704 and the filter/trap module 760 as a unit from the ventilator.

In a second, contagious patient position 794, the contamination control latch 790 fixes the valve module 704 to the filter/trap module 760 so that the filter/trap module 760 can not be removed from the ventilator without either removing the valve module 704 or changing the latch position 790. This requires the removal of the valve module 704 and the filter/trap module 760 as a unit through the removal of the valve module 704 from the actuator module 702.

In practice, the contamination control latch 790 may be effected by any one of a number of different designs. For example, a sliding member may be provided on the valve module 704 that has two positions in which each position engages complimentary tabs or openings on one or the other of the actuator module 702 and the filter/trap module 760. Fasteners, clamps and locking devices are well known in the art and any suitable mechanism may be used herein. Although a single latch mechanism is preferred, multiple independent mechanisms such as sliding members, claps, or knobs may also be used.

In an embodiment of the contamination control latch 790 a visual indicator is provided to indicate to the operator which position, the non-contagious patient position 792 or contagious patient position 794, the assembly 700 is currently in. This may be accomplished in many different ways depending on the particular design selected to perform the function of the contamination control latch 790. For example, if a sliding member is used as described above, when in the contagious patient position 794 a visual indicia (e.g., text such as "Contagious Patient" or a biohazard symbol on a yellow field) may be displayed which is covered by the member when in the non-contagious patient position 792.

Variations and other features associated with the contamination control latch 790 may be provided. For example, in another embodiment the latch 790 may be provided with a third position 796, which allows the all components of the assembly 700 to be freely installed or removed. In yet another embodiment, a mechanical or electrical mechanism may be provided to ensure that a position selection is consciously made by the operator. For example, a prompt during filter change or new patient setup operation may be presented on the operator via the ventilator's user's interface requiring the operator to indicate that the latch 790 has been placed in the proper position prior to the delivery of ventilation. Alternatively, the mechanism may be designed such that the components of the exhalation valve assembly 700 may not be completely installed until a latch 790 position is selected. Other methods and designs related to ensuring that a latch position 792, 794 is selected may also be used.

In an embodiment, the latch 790 can set to the appropriate configuration 792, 794 at any time after it has been installed on the ventilator. This allows the operator to set the latch position after the initiation of ventilation and the status of the patient has been confirmed. Usually, the ventilator is used in a ward setting and the filter/trap modules are cleaned or disposed of in some remoter service area. The latch 790 system described herein provides several benefits in that it not only prevents potentially contaminated parts from being retained on the ventilator it also provides a visual indicator to service personnel remote from the ward of the status of the patient that was associated with the component they are handling. Thus, the latch 790 ensures that the filter/trap module comes apart in a way that is appropriate to the circumstances and alerts the service personnel of the condition of the patient associated with the module.

Figure 8A:
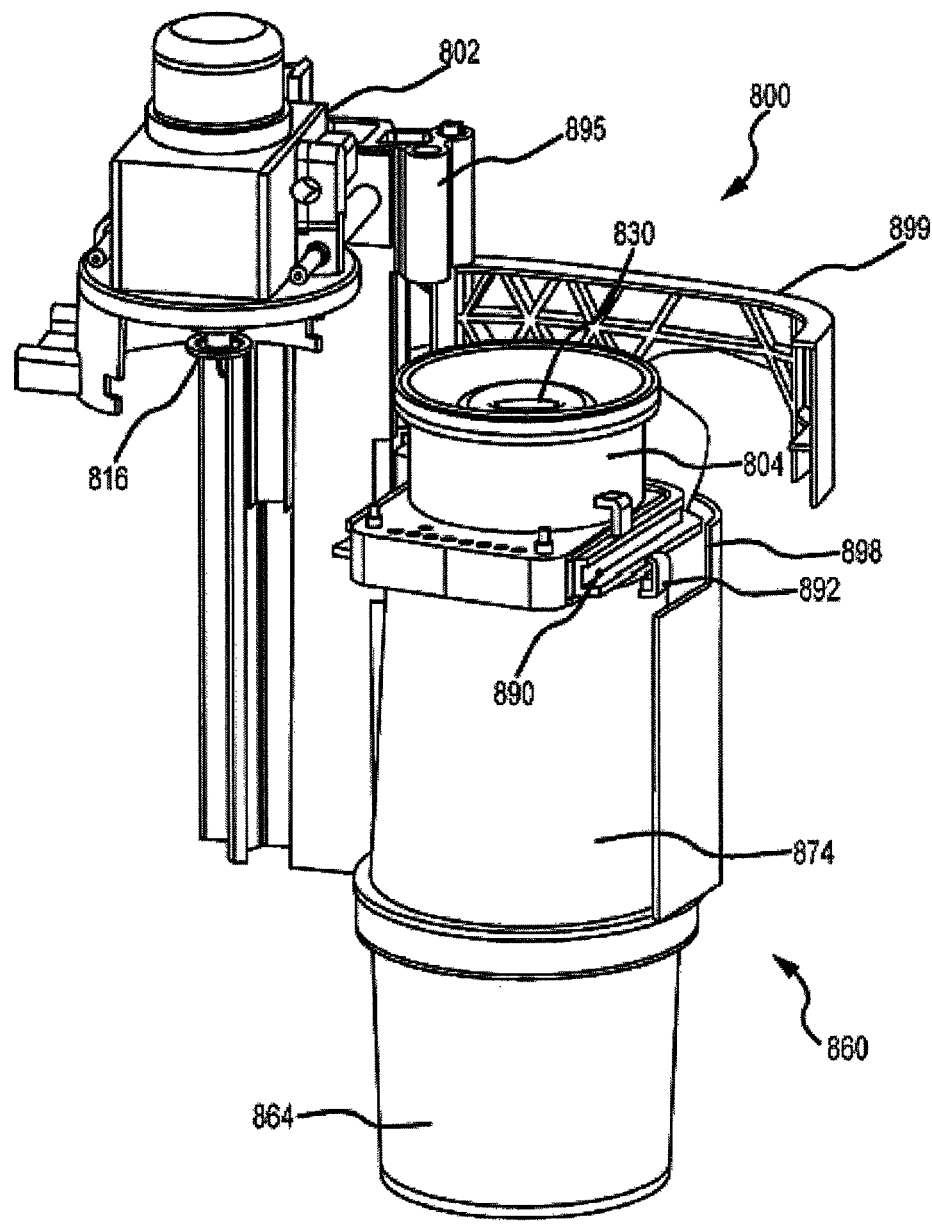
FIG. 8a illustrates the embodiment in a contagious configuration in which the contamination control latch is set to a contagious position and in which the valve module and filter/trap module are shown as a connected assembly removed from the actuator module which would be fixed to the ventilator housing (not shown).
Figure 8B:
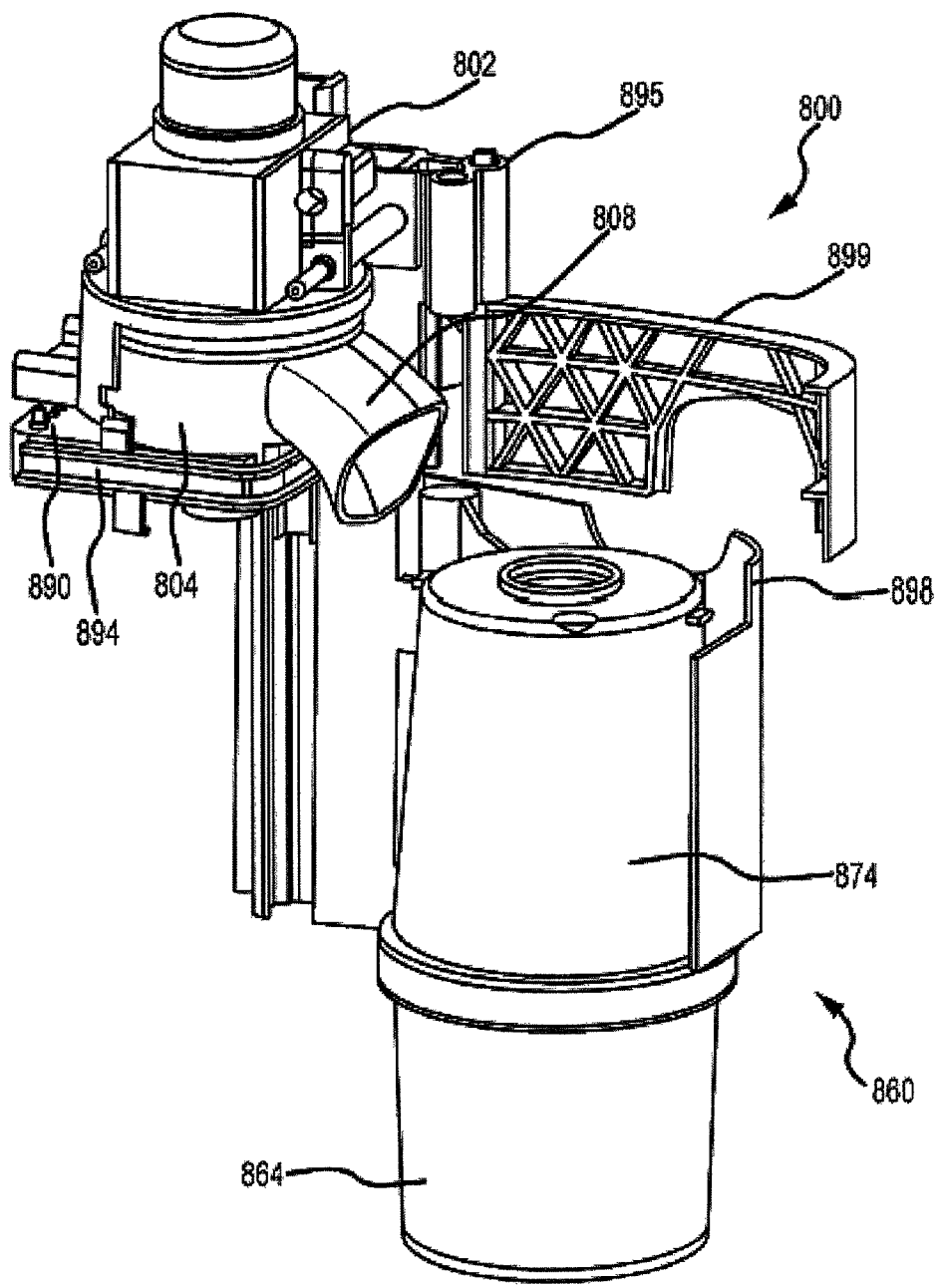
FIG. 8b illustrates the same embodiment as FIG. 8a, but in the non-contagious configuration in which the filter body is illustrated as being separated from the now-latched valve module and actuator module assembly.

FIGS. 8a-8b illustrate an embodiment of an exhalation valve assembly 800 for controlling pressure in a ventilation system. FIG. 8a illustrates the embodiment in a contagious configuration in which the contamination control latch 890 is set to a contagious position 892 and in which the valve module 804 and filter/trap module 860 are shown as a connected assembly removed from the actuator module 802 which would be fixed to the ventilator housing (not shown). FIG. 8a illustrates the actuator module 802 and poppet 816. The filter/trap module 860 is illustrated as latched to the valve module 804.

In the embodiment a cover 898 is illustrated as a built in component of the filter body that, in conjunction with the shape of the ventilator housing, creates an insulating space around the portion of the filter body 874 defining the filter chamber. In addition to the cover integral to the filter body 874, a second hinged cover 899 is illustrated attached to the ventilator housing 895. The second hinged cover 899 opens to reveal the location within the ventilator housing 895 into which the valve module 804 is installed. Both covers are provided with an opening complementary to the outlet port 808 of the valve module 804, which is most clearly illustrated by FIG. 8b.

The condensate trap 864 is illustrated connected to the filter body 874. The seal element 830 is illustrated including a separate seal portion in the center of the seal element and diaphragm that flexibly connects the seal portion to the valve body.

FIG. 8b illustrates the same embodiment as FIG. 8a, but with the contamination control latch 894 in the non-contagious 894 configuration in which the filter body 874 is illustrated as being separated from the now-connected valve module 804 and actuator module 802 assembly.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. For example, the operations and steps of the embodiments of methods described herein may be combined or the sequence of the operations may be changed while still achieving the goals of the technology. In addition, specific functions and/or actions may also be allocated in such as a way as to be performed by a different module or method step without deviating from the overall disclosure. In other words, functional elements being performed by a single or multiple components, in various combinations of hardware and software, and individual functions can be distributed among software applications. In this regard, any number of the features of the different embodiments described herein may be combined into one single embodiment and alternate embodiments having fewer than or more than all of the features herein described are possible.

While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the appended claims.

Unless otherwise indicated, all numbers expressing quantities, properties, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

What is claimed is:

1. An exhalation valve assembly for controlling pressure in a ventilation system comprising:
    a valve module comprising a valve body and attached seal element, the valve body defining an inlet port allowing gas to enter a valve chamber and an exhaust port allowing gas to exit the valve chamber, the valve body having a valve seat opposite the seal element wherein displacement of the seal element relative to the valve seat controls gas pressure within the inlet port, wherein all gas that enters the inlet port exits the exhaust port;
    an actuator module fixed to a ventilator housing and removably connectable to the valve module and, when attached to the valve module, that is operable to move the seal element relative to the valve seat to control the pressure of gas in the inlet port and the release of gas via the exhaust port; and
    a flow sensor contained in the valve body monitoring the flow of gas between the inlet port and the valve seat, wherein all gas entering the inlet port and exiting the exhaust port is monitored by the flow sensor.

2. The exhalation valve assembly of claim 1, wherein a portion of the valve body is moveable to provide access to the flow sensor and removal of the flow sensor.

3. The exhalation valve assembly of claim 1, wherein the valve body further includes at least one pressure sensor port.

4. The exhalation valve assembly of claim 3, wherein the valve body further includes a first pressure sensor port between the inlet port and the valve seat and a second pressure sensor port between the valve seat and the exhaust port.

5. The exhalation valve assembly of claim 1, wherein the actuator module is positioned vertically above the valve module.

6. The exhalation valve assembly of claim 1, wherein the actuator module includes an actuator controlling displacement of or force on a poppet that engages the seal element of the valve module.

7. The exhalation valve assembly of claim 1, wherein the seal element is removably connected to the removable valve body, such that when removed the valve chamber can be accessed for cleaning.

8. The exhalation valve assembly of claim 1, wherein gas flows from the inlet port through the valve seat into the valve chamber and displacement of the seal element effects the flow of gas into the valve chamber.

9. The exhalation valve assembly of claim 1, further comprising a removable filter module attached to the valve module that filters gas prior to entry into the inlet port.

10. A respiratory ventilation system comprising:
    a pressure delivery system;
    an inspiratory limb that receives respiratory gas from the pressure delivery system and delivers the respiratory gas to a patient interface;
    an expiratory limb that receives exhaled gas from the patient interface;
    a valve module comprising a valve body and attached seal element, the valve body defining an inlet port that receives the exhaled gas from the expiratory limb and directs it through a valve seat to a valve chamber and an exhaust port allowing exhaled gas to exit the valve chamber, wherein all gas that enters the inlet port exits the exhaust port, the valve seat opposite the attached seal element wherein displacement of the seal element relative to the valve seat controls gas pressure within the expiratory limb;
    an actuator module fixed to a ventilator housing and removably connected to the valve module and, when attached to the valve module, is operable to move the seal element relative to the valve seat to control the pressure of gas in the inlet port and the release of gas via the exhaust port; and
    a flow sensor contained in the valve body monitoring the flow of gas between the inlet port and the valve seat, wherein all gas entering the inlet port and exiting the exhaust port is monitored by the flow sensor.

11. The respiratory ventilation system of claim 10, wherein a portion of the valve body is moveable to provide access to the flow sensor and removal of the flow sensor.

12. The respiratory ventilation system of claim 10, wherein the valve body further includes at least one pressure sensor port.

13. The respiratory ventilation system of claim 10, wherein the actuator module fixed to a housing containing the pressure delivery system such that the actuator module is positioned vertically above the removable valve module.

14. The respiratory ventilation system of claim 10, wherein the seal element is removably connected to the removable valve body, such that when removed the valve chamber can be accessed for cleaning.

15. The respiratory ventilation system of claim 10, wherein gas flows from the expiratory limb into the inlet port through the valve seat into the valve chamber based on the force on the seal element relative to the valve seat.

16. A method of controlling pressure in an expiratory limb of a ventilation system comprising:

receiving a patient's exhaled gas from an expiratory limb through an inlet port into a removable valve body connected to the ventilation system, the removable valve body comprising: the inlet port, an exhalation port through which gas is released to the environment, and a surface comprising a seal element, wherein all gas received through the inlet port is released through the exhalation port;

displacing a member external to the removable valve body that interfaces with the seal element on the removable valve body, thereby changing a distance between the seal element and a valve seat in the removable valve body and controlling the pressure of the exhaled gas in the expiratory limb; and monitoring the flow of gas with a flow meter located between the inlet port and the valve seat of the removable body, wherein all gas entering through the inlet port and released through the exhalation port is monitored by the flow meter.

17. The method of claim 16 further comprising:

transmitting the monitored flow of gas to a processor of the ventilation system controlling the delivery of gas to the patient.

18. The method of claim 16 further comprising:

monitoring a difference in pressure between the exhaled gas in the ventilation system on the expiratory limb-side of the valve seat and a gas pressure of the environment or the valve chamber.

19. The method of claim 18 further comprising:

calculating a first flow measurement from the difference in pressure and the distance between the seal element and the valve seat; and performing an action related to the delivery of gas to the patient based on a comparison of the first flow measurement and the monitored flow of gas from the flow meter.

20. The method of claim 18 wherein performing an action comprises one or more of indicating an alarm condition, changing a pressure of gas delivered to the patient based on the comparison of the first flow measurement and the monitored flow of gas from the flow meter, and changing a flow of gas delivered to the patient based on the comparison of the first flow measurement and the monitored flow of gas from the flow meter.

* * * * *